US012558689B2

(12) United States Patent
Daniele et al.

(10) Patent No.: US 12,558,689 B2
(45) Date of Patent: Feb. 24, 2026

(54) VASCULAR DEVELOPMENT MONITORING SYSTEMS AND USES THEREOF

(71) Applicant: North Carolina State University, Raleigh, NC (US)

(72) Inventors: Michael Daniele, Raleigh, NC (US); Patrick D. Erb, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 966 days.

(21) Appl. No.: 16/979,994

(22) PCT Filed: Mar. 12, 2019

(86) PCT No.: PCT/US2019/021816
§ 371 (c)(1),
(2) Date: Sep. 11, 2020

(87) PCT Pub. No.: WO2019/178073
PCT Pub. Date: Sep. 19, 2019

(65) Prior Publication Data
US 2021/0008555 A1 Jan. 14, 2021

Related U.S. Application Data

(60) Provisional application No. 62/641,591, filed on Mar. 12, 2018.

(51) Int. Cl.
*B01L 3/00* (2006.01)
*C12M 1/00* (2006.01)
(Continued)

(52) U.S. Cl.
CPC ....... *B01L 3/502776* (2013.01); *C12M 23/16* (2013.01); *C12M 23/40* (2013.01);
(Continued)

(58) Field of Classification Search
None
See application file for complete search history.

(56) References Cited

U.S. PATENT DOCUMENTS 6,916,397 B2 7/2005 Pfeiffer et al.
7,402,154 B2 7/2008 Holst et al.
(Continued)

FOREIGN PATENT DOCUMENTS

WO 2014/031532 A1 2/2014

OTHER PUBLICATIONS

Hsu et al., "A microfluidic platform for generating large-scale nearly identical human microphysiological vascularized tissue arrays", May 2013, Lab Chip, 13, 2990-2998 (Year: 2013).*
(Continued)

*Primary Examiner* — Henry H Nguyen
(74) *Attorney, Agent, or Firm* — Thomas|Horstemeyer, LLP

(57) ABSTRACT

Described herein are devices and systems that can be configured to and/or capable of monitoring and/or controlling fluid flow within microchannels and/or vessels in a microphysiological model. Described herein are aspects of a system configured to monitor and/or control fluid flow in a microfluidic device that can include a manifold device, where the manifold device can include an inlet reservoir, an outlet reservoir, a pressure jumper, a sensor, and a scaffold block that can have a plurality of microfluidic channels and/or vessels. Also described herein are methods of making and using the systems and devices described herein.

5 Claims, 24 Drawing Sheets

(51) Int. Cl.
    *C12M 1/34*         (2006.01)
    *C12M 3/06*         (2006.01)

(52) U.S. Cl.
    CPC ...... *C12M 41/40* (2013.01); *B01L 2200/0636*
               (2013.01); *B01L 2200/10* (2013.01)

(56)            References Cited

U.S. PATENT DOCUMENTS

| | | | |
|---|---|---|---|
| 9,205,396 B2 | 12/2015 | Arai | |
| 10,114,010 B1 * | 10/2018 | Budhwani | C12M 23/58 |
| 2004/0030277 A1 | 2/2004 | O'Mahony et al. | |
| 2005/0042745 A1 * | 2/2005 | Tsuzuki | C12M 41/40 |
| | | | 435/295.3 |
| 2010/0199750 A1 | 8/2010 | Arnold et al. | |
| 2013/0295598 A1 | 11/2013 | Marx et al. | |
| 2014/0057311 A1 | 2/2014 | Kamm et al. | |
| 2015/0004077 A1 * | 1/2015 | Wikswo | C12M 35/08 |
| | | | 422/502 |
| 2015/0093815 A1 * | 4/2015 | Kiani | F16K 99/0059 |
| | | | 422/503 |
| 2015/0342177 A1 * | 12/2015 | Hassanein | C12M 29/10 |
| | | | 435/284.1 |
| 2016/0130543 A1 | 5/2016 | Daniele et al. | |
| 2018/0142196 A1 * | 5/2018 | Coppeta | C12M 29/00 |

OTHER PUBLICATIONS

Hsu et al., "Full range physiological mass transport control in 3D tissue cultures", Lab Chip, 2013, 13, 81 (Year: 2013).*
Hsu et al., "Supplementary information Full range physiological mass transport control in 3D tissue cultures", Lab Chip, 2013, 13, 81 (Year: 2013).*
International Search Report and Written Opinion for PCT/US2019/021816 mailed on Jul. 17, 2019.
European Search Report for 19768538.1-1132 mailed on Nov. 12, 2021.

M. A. Daniele, "Interpenetrating networks based on gelatin methacrylamide and PEG formed using concurrent thiol click chemistries for hydrogel tissue engineering scaffolds," Biomaterials, vol. 35, pp. 1845-1856, Feb. 2014.
M. R. Zanotelli, et al., "Stable engineered vascular networks from human induced pluripotent stem cell-derived endothelial cells cultured in synthetic hydrogels," Acta Biomater, vol. 35, pp. 32-41, Apr. 15, 2016.
Y. Zheng, et al., "In vitro microvessels for the study of angiogenesis and thrombosis," Proc Natl Acad Sci U S A, vol. 109, pp. 9342-9347, Jun. 12, 2012.
S. A. Roberts, et al., "Microvessel manifold for perfusion and media exchange in three-dimensional cell cultures," Biomicrofluidics, vol. 10, p. 054109, Sep. 2016.
S. Kim, "Engineering of functional, perfusable 3D microvascular networks on a chip," Lab Chip, vol. 13, pp. 1489-1500, Apr. 21, 2013.
X. Wang, et al., "Engineering anastomosis between living capillary networks and endothelial cell-lined microfluidic channels," Lab Chip, vol. 16, pp. 282-290, Jan. 21, 2016.
W. Zhang, et al., "Elastomeric free-form blood vessels for interconnecting organs on chip systems," Lab Chip, vol. 16, pp. 1579-86, Apr. 26, 2016.
Y. S. Zhang, F. Davoudi, p. Walch, A. Manbachi, X. Luo, V. Dell'Erba, et al., "Bioprinted thrombosis-on-a-chip," Lab Chip, vol. 16, pp. 4097-4105, Oct. 18, 2016.
H. Lee, et al., "Microvasculature: An essential component for organ-on-chip systems," MRS Bulletin, vol. 39, pp. 51-59, 2014.
J. S. Miller, et al., "Rapid casting of patterned vascular networks for perfusable engineered three-dimensional tissues," Nat Mater, vol. 11, pp. 768-774, Sep. 2012.
M. L. Moya, Y. H. Hsu, A. P. Lee, C. C. Hughes, and S. C. George, "In vitro perfused human capillary networks," Tissue Eng Part C Methods, vol. 19, pp. 730-737, Sep. 2013.
J. A. Whisler, et al., "Control of perfusable microvascular network morphology using a multiculture microfluidic system," Tissue Eng Part C Methods, vol. 20, pp. 543-552, Jul. 2014.

\* cited by examiner vascular          scaffold          jumper
volume, $V_v$  $\propto$  resistance, $R_h$  $\propto$  flow rate, $Q_j$

| Device | Vascular Volume | Lumped Element Jumper Q | COMSOL Jumper Q |
|---|---|---|---|
| Original Branches | 2.1% | 448.3 | 456.3 |
| Eight Connections | 2.8% | 428.5 | 432.2 |
| Sixteen Connections | 3.6% | 400.8 | 414.6 |

FIG. 5

| Device | SU-8 Height (um) * | Theoretical Jumper Q (uL/min) ** | Experimental Jumper Q (uL/min) |
|---|---|---|---|
| Original Branches | 198.9 ± 37.2 | 370.2 ± 85.4 | 368.3 ± 12.7 |
| Eight Connections | 221.1 ± 33.4 | 293.1 ± 53.6 | 220.4 ± 7.0 |
| Sixteen Connections | 253.0 ± 29.2 | 209.5 ± 36.8 | 135.2 ± 2.6 |
| Split Once | 243.8 ± 42.6 | 183.4 ± 44.6 | 133.3 ± 2.4 |
| Split Twice | 223.4 ± 31.1 | 238.3 ± 44.1 | 163.2 ± 4.1 |
| Sparse Angiogenesis | 190.9 ± 44.6 | 336.8 ± 93.5 | 354.3 ± 12.6 |
| Minor Angiogenesis | 214.4 ± 37.1 | 264.9 ± 58.9 | 261.2 ± 11.0 |

* SU-8 height is a measurable parameter of a physical device, and is inversely related to scaffold resistance

** Theoretical data has standard deviation because it incorporates the range of SU-8 height measured for each device respectively

FIG. 6

VASCULAR DEVELOPMENT MONITORING SYSTEMS AND USES THEREOF

CROSS-REFERENCE TO RELATED APPLICATIONS

This application is the 35 U.S.C. § 371 national stage entry of PCT Application No. PCT/US2019/021816, filed Mar. 12, 2019, where the PCT claims priority to, and the benefit of, U.S. provisional application entitled "VASCU-LAR DEVELOPMENT MONITORING SYSTEMS AND USES THEREOF" having Ser. No. 62/641,591, filed Mar. 12, 2018, both of which are incorporated herein by reference in their entireties.

BACKGROUND

Microphysiological models have the potential to eliminate the use of animals for pharmaceutical testing, immune response testing, and disease modeling. However, most microphysiological models, also known as organ-on-chip devices, lack the necessary vasculature needed to correctly recapitulate organ systems in vitro. As such, there exists a need for improved microphysiological model system, devices, and techniques.

SUMMARY

Described herein are aspects of a system configured to monitor and/or control fluid flow in a microfluidic device, the system comprising: a manifold device that can include an inlet reservoir, wherein the inlet reservoir has an inlet configured to receive a fluid flow; an outlet reservoir, wherein the outlet reservoir has an outlet configured to drain a fluid flow from the manifold device; a pressure jumper; wherein the pressure jumper is coupled to the inlet reservoir and the outlet reservoir; a sensor, wherein the sensor is coupled to the jumper; and a scaffold block having a plurality of microfluidic channels and/or vessels configured to transport a fluid, wherein one or more of the plurality of microfluidic channels and/or vessels is coupled to the inlet reservoir and/or the outlet reservoir; and a pump, wherein the pump is coupled to the inlet and the outlet of the manifold device.

The system can further include a computer configured to receive and analyze data from the sensor; wherein the computer can be coupled to the sensor of the manifold device. The computer can be coupled to the pump, wherein the computer can be further configured to transmit a signal to the pump, wherein the computer can be further configured to control a flow rate of fluid through the manifold device via control of the pump. The system can be configured to monitor fluid flow through the system in real-time. The hydrodynamic resistance in the pressure jumper can be greater than the hydrodynamic resistance in the inlet reservoir and/or outlet reservoir.

The system can be configured to generate a decrease in fluid flow rate in the pressure jumper in response to an increase in the number of microfluidic channels and/or vessels in the plurality of microfluidic channels and/or vessels of the manifold device. The system can be configured to generate an increase in fluid flow rate in the pressure jumper in response to a decrease in the number of microfluidic channels and/or vessels in the plurality of microfluidic channels and/or vessels of the manifold device. The system can be configured to maintain a specific fluid pressure within the system in response to changes in fluid flow rate through the pressure jumper. The sensor can be configured to measure a fluid flow rate. The sensor is configured to measure pressure.

Also described herein are aspects of a manifold device configured to contain a fluid that can include an inlet reservoir, wherein the inlet reservoir has an inlet configured to receive a fluid flow; an outlet reservoir, wherein the outlet reservoir has an outlet configured to drain a fluid flow from the manifold device; a pressure jumper; wherein the pressure jumper can be coupled to the inlet reservoir and the outlet reservoir; a sensor, wherein the sensor can be coupled to the pressure jumper; and a scaffold block having a plurality of microfluidic channels and/or vessels configured to transport a fluid, wherein one or more of the plurality of microfluidic channels and/or vessels is coupled to the inlet reservoir and/or the outlet reservoir. The sensor can be configured to measure fluid flow rate. The sensor can be configured to measure pressure.

Also described herein are aspects of a method of monitoring and/or controlling fluid flow through a microphysiological model system, that can include the step(s) of flowing a fluid continuously through a manifold device, wherein the manifold device comprises: an inlet reservoir, wherein the inlet reservoir has an inlet configured to receive a fluid flow; an outlet reservoir, wherein the outlet reservoir has an outlet configured to drain a fluid flow from the manifold device; a pressure jumper; wherein the jumper is coupled to the inlet reservoir and the outlet reservoir; a sensor, wherein the sensor is coupled to the pressure jumper; and a scaffold block having a plurality of microfluidic channels and/or vessels configured to transport a fluid, wherein one or more of the plurality of microfluidic channels and/or vessels is coupled to the inlet reservoir and/or the outlet reservoir; sensing a fluid flow rate through the pressure jumper via the sensor; and altering the fluid flow rate through the manifold device such that a desired shear stress and/or pressure within the plurality of microfluidic channels and/or vessels in the manifold device. The method can further include the step of quantifying an amount of angiogenesis of vessels in the manifold device via the step of sensing the fluid flow rate through the pressure jumper. In some aspects, the sensor is configured to measure pressure. In some aspects, the step of sensing is conducted in real time.

Also described herein are aspects of a method to quantify angiogenesis in a microphysiological model system, that can include the step of flowing a fluid continuously through a manifold device, wherein the manifold device comprises: an inlet reservoir, wherein the inlet reservoir has an inlet configured to receive a fluid flow; an outlet reservoir, wherein the outlet reservoir has an outlet configured to drain a fluid flow from the manifold device; a pressure jumper; wherein the jumper is coupled to the inlet reservoir and the outlet reservoir; a sensor, wherein the sensor is coupled to the pressure jumper; and a scaffold block having a plurality of microfluidic channels and/or vessels configured to transport a fluid, wherein one or more of the plurality of microfluidic channels and/or vessels is coupled to the inlet reservoir and/or the outlet reservoir; sensing a fluid flow rate through the pressure jumper via the sensor; and altering the fluid flow rate through the manifold device such that a desired shear stress and/or pressure within the plurality of microfluidic channels and/or vessels in the manifold device. The sensor can be configured to measure pressure. The step of sensing can be conducted in real time. In some aspects a decrease in fluid flow rate in the pressure jumper corresponds to an increase in the number of microfluidic channels and/or vessels in the plurality of microfluidic channels and/or vessels of the manifold device. In some aspects an increase in fluid flow rate in the pressure jumper corresponds to a decrease in the number of microfluidic channels and/or vessels in the plurality of microfluidic channels and/or vessels of the manifold device.

BRIEF DESCRIPTION OF THE DRAWINGS

Further aspects of the present disclosure will be readily appreciated upon review of the detailed description of its various embodiments, described below, when taken in conjunction with the accompanying drawings.

(FIG. 1B) Top down view of vascularized scaffold region changing over time, (FIG. 1C) Prototype device without sensor demonstrating complete device, (FIG. 1D) Alternate view of the same device, (FIG. 1E) Graphical representation of the relationship between system variables and outputs over time.

FIG. 5 shows a table that can demonstrate cylindrical cross section channels.

FIG. 6 shows a table that can demonstrate Rectangular Cross Section Channels

DETAILED DESCRIPTION

Figure 1A:
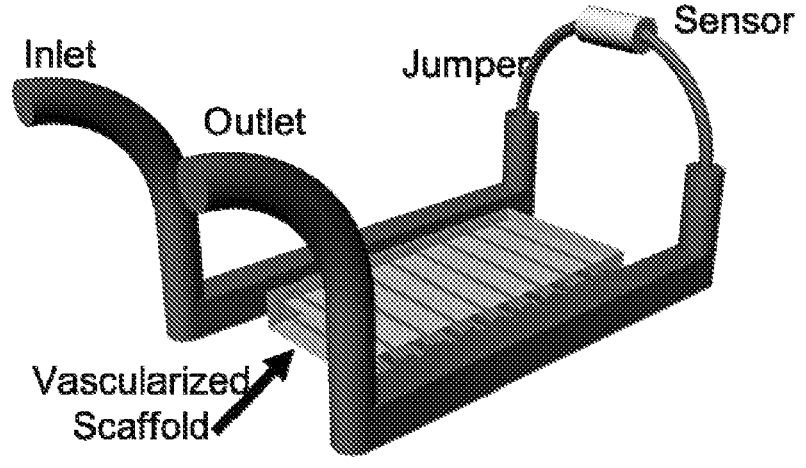
FIGS. 1A-1E show (FIG. 1A) a 3D rendered model of the manifold device with jumper and sensor.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 0.5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, 2-D culture systems, 3-D culture systems, microphysiological modeling, physiology, physics, computer science, organic chemistry, and biochemistry, like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Discussion

Microphysiological models have the potential to eliminate the use of animals for pharmaceutical testing, immune response testing, and disease modeling. However, most microphysiological models, also known as organ-on-chip devices, lack the necessary vasculature needed to correctly recapitulate organ systems in vitro. Blood vessels play a vital role in organ function and must be included if questions about physiological phenomena of the biology, chemistry, and physics of these organs are to be addressed. Moreover, control of the vascularized microphysiological model is paramount to the success of these devices in the clinic. A major limitation of current microphysiological models is that they are often 2-D and rely on diffusion of fluids and thus do not accurately represent a complex tissue or organ and they fail to incorporate dynamic, vascularized tissue constructs with realistic geometries, flow rates, and supporting cell types. These limitations are due, at least in part, to the lack of the ability to monitor, measure, and/or control the fluid flow through the vasculature in the microphysiological model.

With that said, described herein are devices and systems that can be configured to and capable of monitoring and/or controlling fluid flow through microfluidic channels and/or vessels in a microphysiological model. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Figure 4:
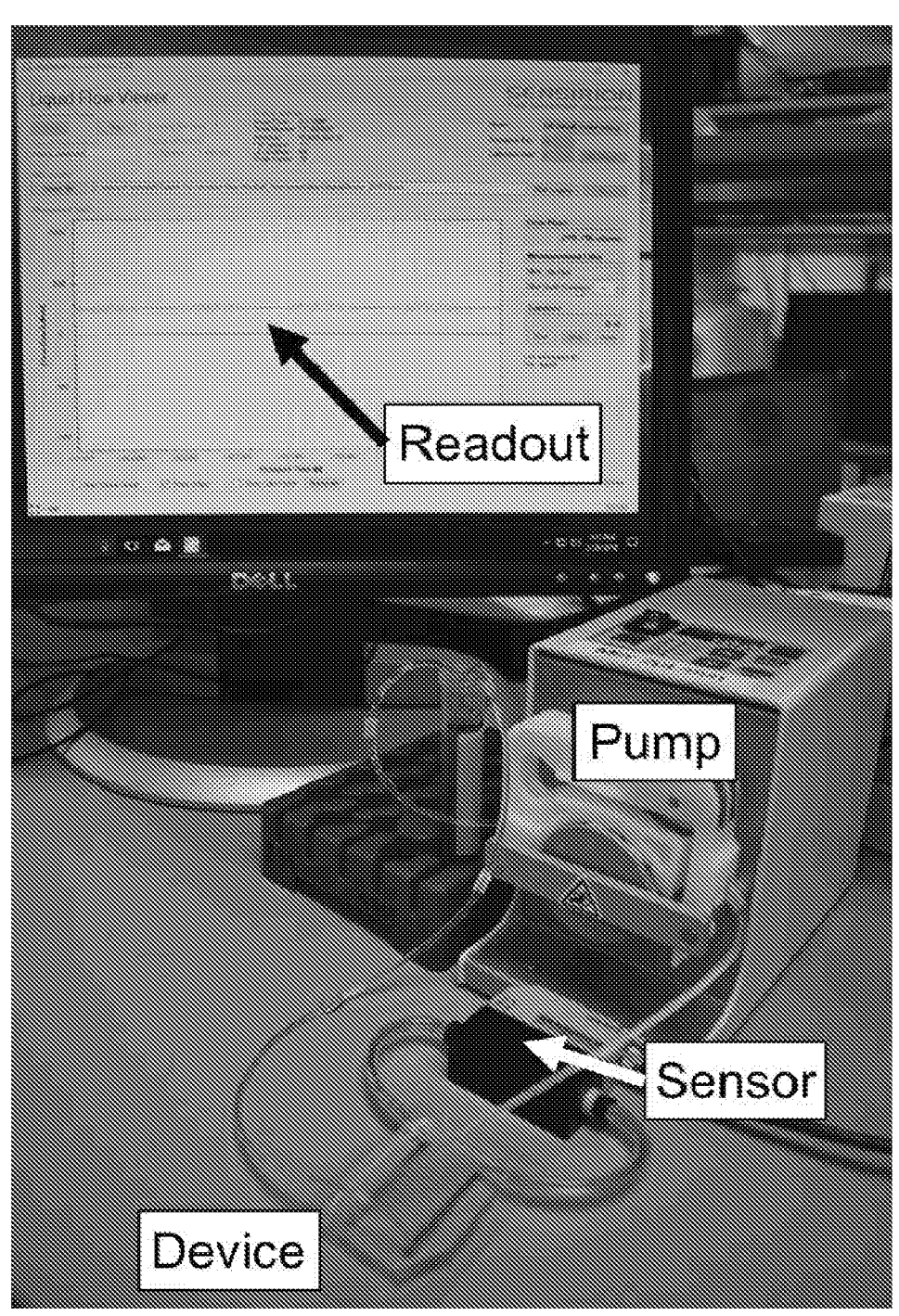
FIG. 4 shows operation of vascular monitoring system manifold device.
Figure 11:
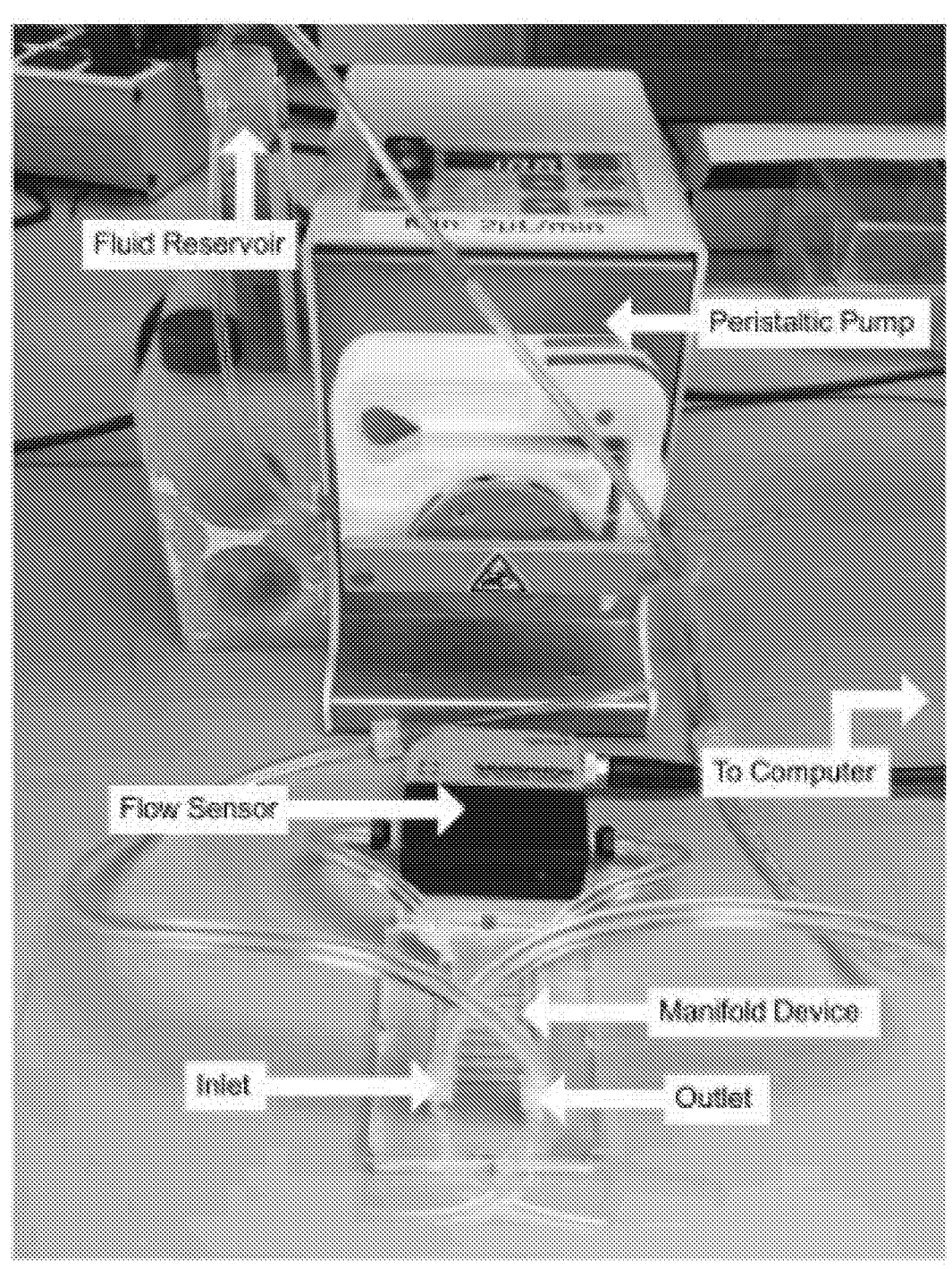
FIG. 11 shows an image of a mock manifold device under operation, complete with a flow sensor on the jumper and a peristaltic pump for fluid flow from the inlet to the outlet.
Figure 13:
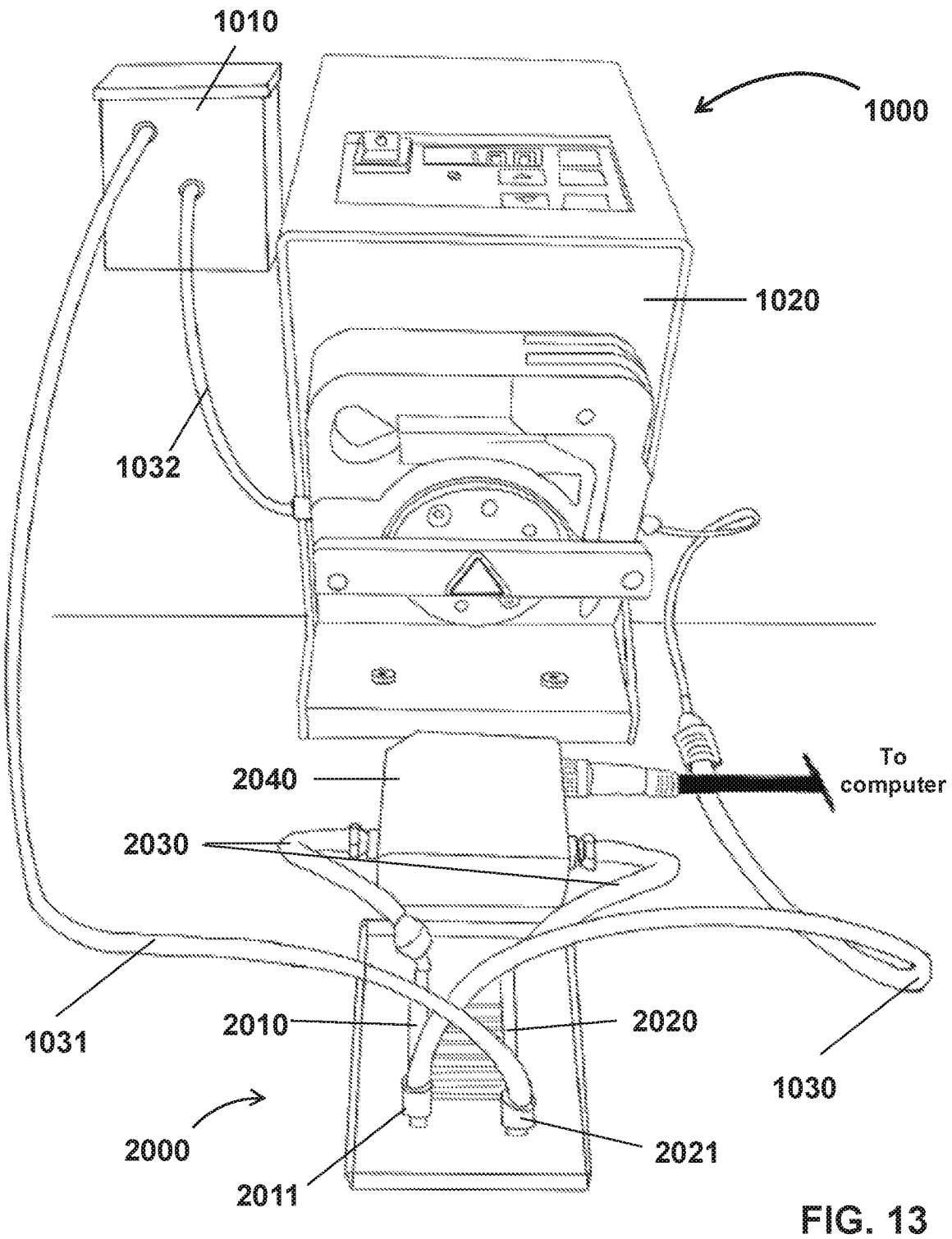
FIG. 13 shows an embodiment of a vascular monitoring system as described herein.
Figure 14:
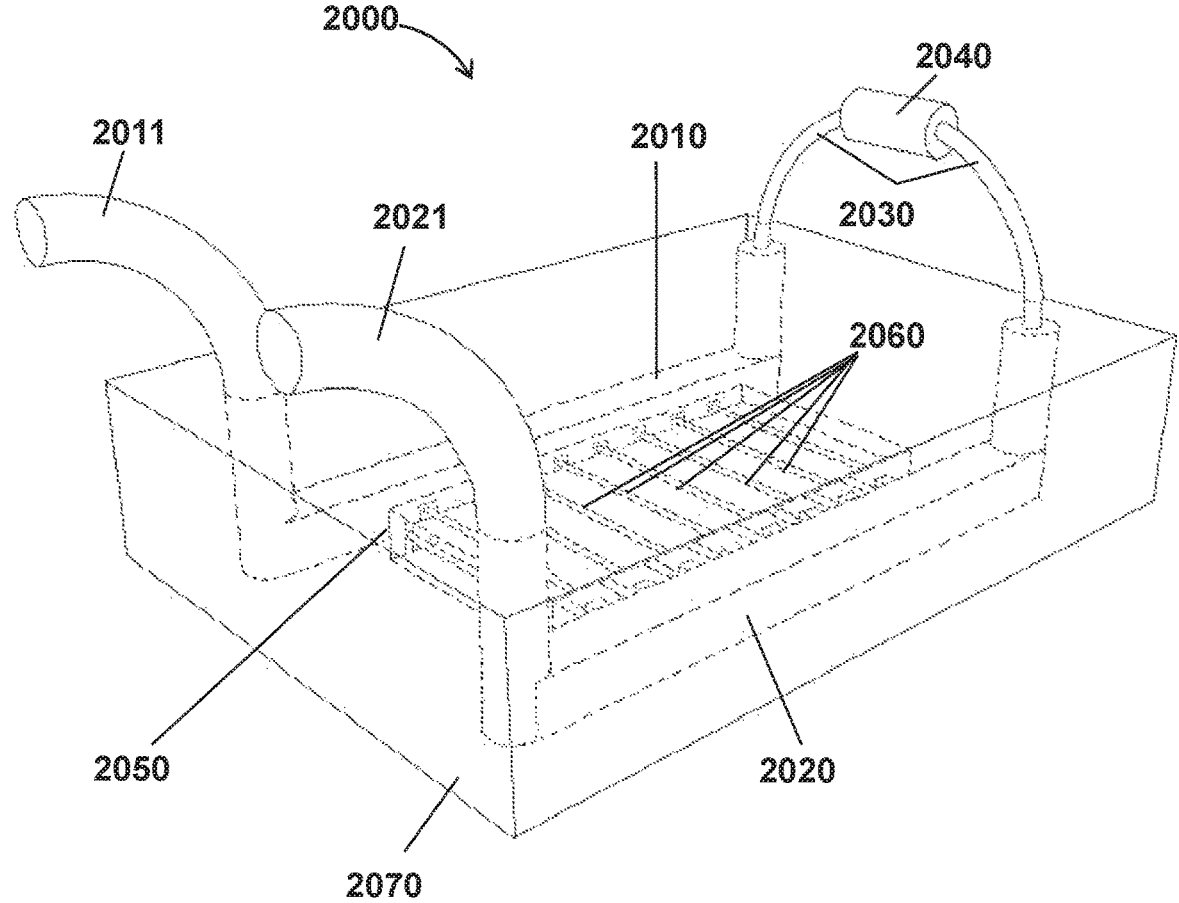
FIG. 14 shows an embodiment of a manifold device as described herein.
Figure 15:
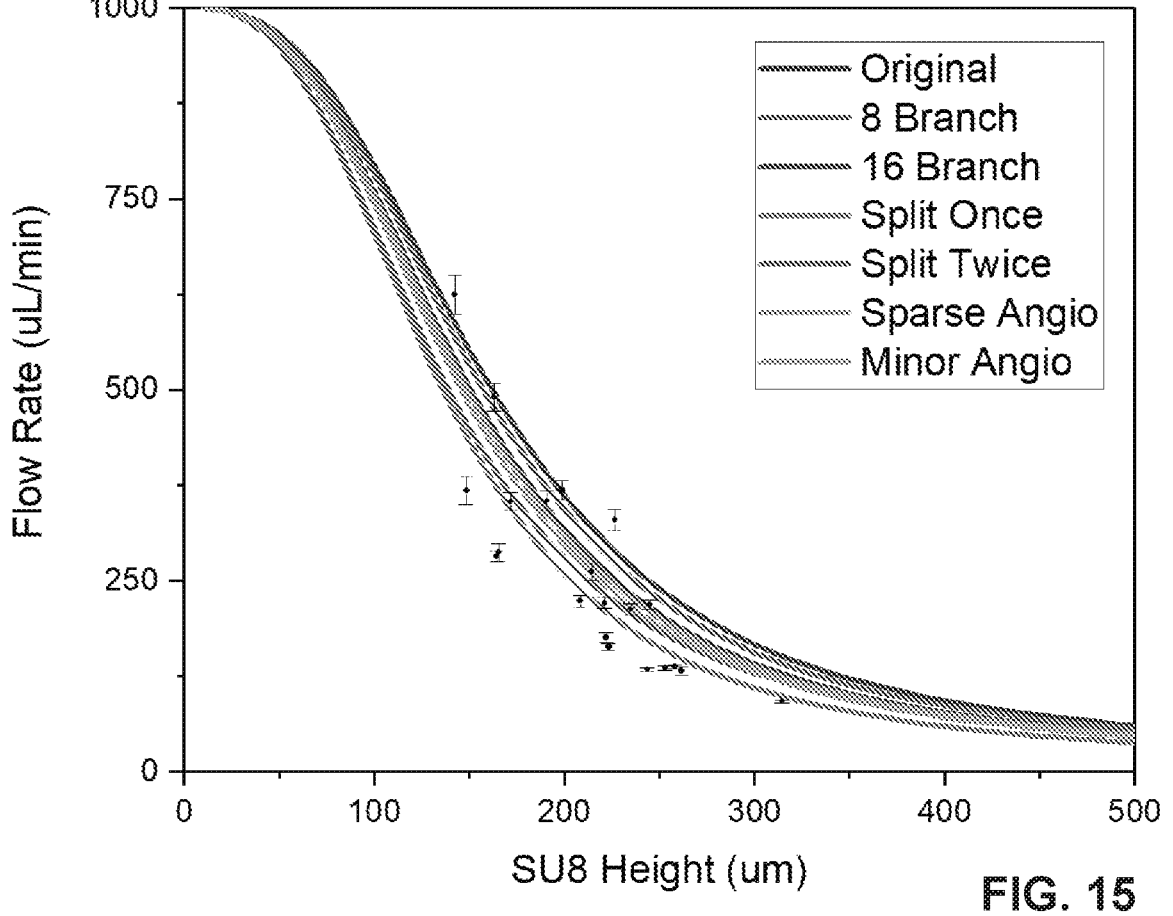
FIG. 15 shows theoretical curves and experimental data points of a group of embodiments of a manifold device as described herein.

With the general description of aspects of the system and device in mind, attention is directed to e.g. FIGS. 4, 11, and 13 which can show various embodiments of a system 1000 configured to monitor and/or control various aspects of fluid flow in a microfluidic device (e.g. a manifold device 2000 described herein). The system 1000 can include a manifold device 2000 (see also e.g., FIGS. 1A, 1C, 1D and 14) that can include an inlet reservoir 2010, wherein the inlet reservoir 2010 can have an inlet 2011 configured to receive a fluid flow; an outlet reservoir 2020, wherein the outlet reservoir 2020 can have an outlet 2021 configured to drain a fluid flow from the manifold device 2000; a pressure jumper 2030; wherein the pressure jumper 2030 can be coupled to the inlet reservoir 2010 and the outlet reservoir 2020; a sensor 2040, wherein the sensor 2040 can be coupled to the jumper 2030; and a scaffold block 2050 that can have a plurality of microfluidic channels and/or vessels 2060 configured to transport a fluid, wherein one or more of the plurality of microfluidic channels and/or vessels 2060 can be coupled to the inlet reservoir 2010 and/or the outlet reservoir 2020; and a pump 1020, wherein the pump 1020 can be coupled to the inlet 2011 and the outlet 2021 of the manifold device 2000. The pump 1020 can be any device or system that is capable of moving and/or driving a fluid. In some embodiments, the pump 1020 can be a peristaltic pump, a coupled syringe pump, gear pump, and/or pneumatic pump. The manifold device 2000 can further contain a housing 2070 that can be configured to couple to one or more components of the manifold device 2000 to hold the components in place relative to each other. Inlet tubing 1030 can couple the pump 1020 to the inlet 2011 and can be configured to hold a fluid flow. Outlet tubing 1031 can couple the outlet 2021 to a fluid reservoir 1010. The fluid reservoir 1010 can be any suitable container that can hold a fluid. The fluid reservoir 1010 can be configured to receive and hold a fluid from the outlet tubing 1031. The system 1000 can further include pump tubing 1032, wherein the pump tubing can couple to the fluid reservoir 1010 and a pump inlet, wherein the pump inlet is configured to receive a fluid from the pump tubing 1032. The pump 1020 can be configured to couple pump tubing 1032 to the inlet tubing 1030. It is also to be understood that "inlet" and "outlet" can be used interchangeably depending on the configuration of system 1000. The system can be run in "forward" or "reverse" fluid flow direction.

The system 1000 can further include a computer configured to receive and analyze data from the sensor 2040; wherein the computer is coupled to the sensor 2040 of the manifold device 2000. The computer can be directly (e.g. via a cable or other wire) or wirelessly coupled (e.g. via Bluetooth protocol or other wireless communication protocol) to the sensor 2040. The computer can contain software configured to analyze input from the sensor 2040 and provide an output regarding sensor data (see e.g. FIG. 4 (readout)). Suitable software programs will be appreciated by those of skill in the art and can include LabVIEW, C++, Java, Python, MATLAB, and/or any independently created program that may or may not leverage commercial packages. In short, calculation, manipulation, control, and/or feedback of device parameters and/or sensor readouts and data can be completed via LabVIEW, C++, Java, Python, MATLAB, and/or any independently created program that may or may not leverage commercial packages.

Figure 1B:
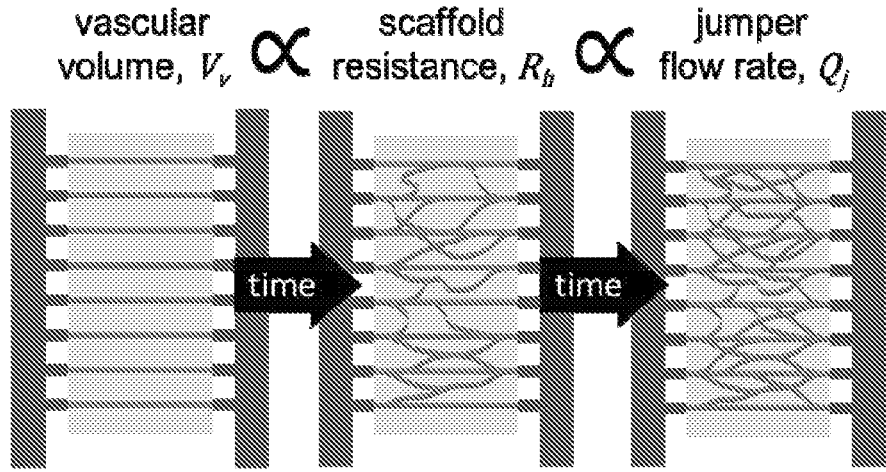
Figure 1C:
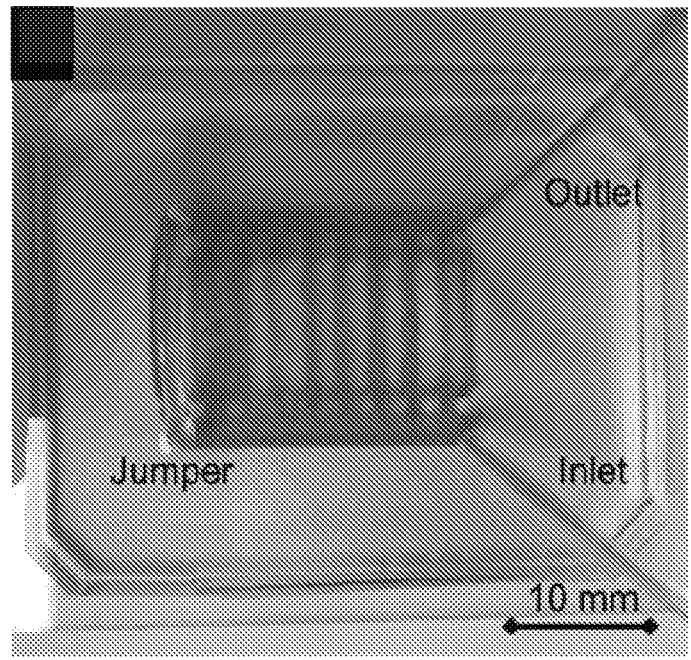
Figure 1D:
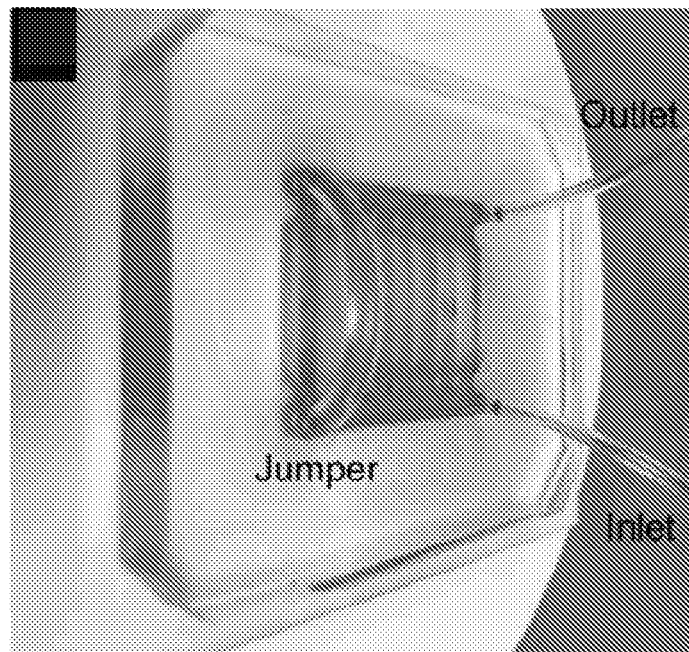
Figure 1E:
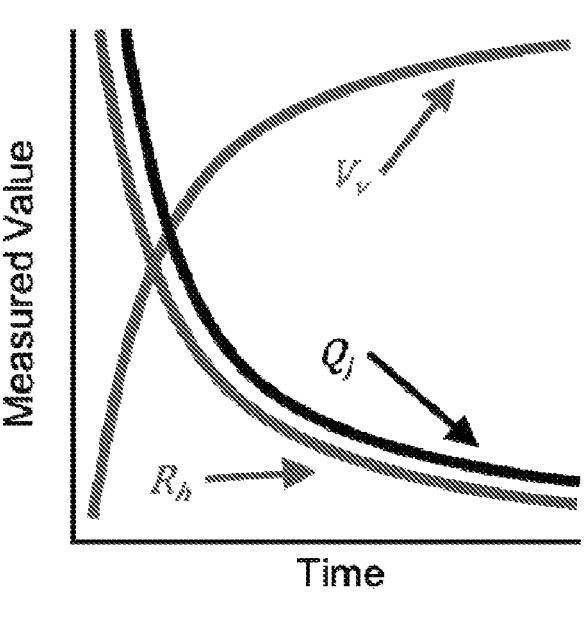

The computer can be coupled to the pump 1020, wherein the computer can be further configured to transmit a signal to the pump 1020, wherein the computer can be further configured to control a flow ate, and/or pressure, and/or other fluid characteristic of a fluid through the manifold device 2000 via control of the pump 1020. In short the computer can be configured to obtain input from the sensor 2040 and provide control of the pump 1020 such that the flow rate of fluid through the manifold device 2000 is altered (increased or decreased as necessary) to maintain a desired rate through the manifold device 2000, particularly through the microfluidic channels and/or vessels 2060. The flow rate is predetermined such that a specific shear stress or pressure is maintained in the microfluidic channels and/or vessels 2060 in the manifold device 2000. The microfluidic channels and/or vessels 2060 can be linear, branched, or a combination of both. As shown in e.g. FIGS. 1A-1D microchannels and/or vessels 2060 can extend in substantially parallel fashion between the inlet reservoir 2010 and the outlet reservoir 2020. Some microfluidic channels and/or vessels, 2060 such as vessels that can form during angiogenesis in the device (see e.g. FIG. 1B) can form branches that can extend between one or more other microfluidic channels or vessels 2060 (e.g. those extending between the inlet and the outlet reservoirs (2010, 2020) and/or other branched microfluidic channels or vessels 2060).

The system 1000 can be configured to monitor fluid flow through the system 1000 in real-time. In other words, the system 1000 can be configured to monitor fluid flow through the system 1000 as fluid is flowing through the system 1000. Also, the system 1000 can be configured to control fluid flow through the system 1000 in real-time in response to the real-time fluid flow rate or other parameter (e.g. pressure) data. The system 1000 can be configured such that the hydrodynamic resistance in the pressure jumper 2030 is greater than the hydrodynamic resistance in the inlet reservoir 2010 and/or outlet reservoir 2020. The system 1000 can be configured to generate a decrease in fluid flow rate in the pressure jumper 2030 in response to an increase in the number of microfluidic channels and/or vessels 2060 in the plurality of microfluidic channels and/or vessels 2060 of the manifold device 2000. The system 1000 can be configured to generate an increase in fluid flow rate in the pressure jumper 2030 in response to a decrease in the number of microfluidic channels and/or vessels 2060 in the plurality of microfluidic channels and/or vessels 2060 of the manifold device 2000. The system 1000 can be configured to maintain a specific fluid pressure within the system 1000 in response to changes in fluid flow rate through the pressure jumper 2030. The sensor 2040 can be configured to detect and/or measure a parameter of the fluid flowing through the system 1000. The sensor 2040 can be configured to measure a fluid flow rate and/or pressure. Other fluid characteristics of a fluid that is driven through the system 1000 that can be measured include, but are not limited to hydrodynamic resistance, viscosity, density, and compressibility, which may or may not be measured by the sensor 2040. Other suitable methods and devices for measuring any of these characteristics will be appreciated by those of ordinary skill in the art and are within the scope of this disclosure.

Various components of the system 1000, including the manifold device 2000, can be fabricated by any suitable method, including but not limited to injection molding, casting, machining, thermoforming, hot embossing, photopolymerization, and/or 3-D printing. Suitable fabrication methods will be appreciated by those of ordinary skill in the art in view of this disclosure. Further components of the system 1000 can be made out of any suitable material(s). The manifold device 2000 can be fabricated from various natural and synthetic materials as desired. Such natural materials can include cells, tissues, proteins, gelatin, collagen, blood, plasma, serum, culture media, hyaluronic acid, fibronectin, RGD peptide, other natural polymers (e.g. polylactic acid), proteins, peptides, and/or any combination thereof. Suitable synthetic materials can include polymers (e.g. plastics, acrylics, polymethyl ethacrylate, polycarbonate, polydimethylsiloxane, cyclic olefin copolymer, polyethylene glycol, conjugations thereof, and/or co-polymers thereof), co-polymers, metals, ceramics, and/or combinations thereof. In some embodiments, the manifold device 2000 and/or other components of the system 1000 described herein can be biocompatible.

In operation, fluid can be flowed through the manifold device 2000 via a pump 1020. As the fluid passes through the pressure jumper 2030, a sensor 2040 can measure one or more attributes of the fluid in the system at that time (e.g. flow rate and/or pressure). The sensor 2040 can send this information to a computer, which can then analyze the data and provide a report. This process of measuring attributes of the fluid and its flow across the sensor 2040 can thus allow for real time monitoring of the vasculature within the system 1000. In short, the pressure jumper 2030 can be configured such that the hydrodynamic resistance is greater than that of the inlet reservoir 2010 and outlet reservoir 2020. The manifold device 2000 can be configured such that the flow rate of fluid in the pressure jumper 2030 relates to the resistance across the microfluidic channels and/or vessels 2060 in the scaffold block 2050. Specifically, as the resistance (or pressure) across the microfluidic channels and/or vessels 2060 in the scaffold block 2050 decreases, the fluid flow rate across the pressure jumper 2030 also decreases. Conversely, if the resistance (or pressure) across the microfluidic channels and/or vessels 2060 in the scaffold block 2050 increases, the fluid flow rate across the pressure jumper 2030 also increases. The resistance (or pressure) across the microfluidic channels and/or vessels 2060 in the scaffold block 2050 can decrease as the result of increased number of vessels present that the fluid must flow through. This increases the amount of fluid volume of the microfluidic channels and/or vessels 2060 in scaffold block 2050 and results in a decrease in fluid flow rate across the pressure jumper 2030. This can happen if new vessels are formed in the scaffold block 2050 (e.g. angiogenesis occurs). Conversely, if the number of vessels decrease, then the fluid volume of the microfluidic channels and/or vessels 2060 in scaffold block 2050 can decrease, which can lead to an increase in the resistance (or pressure) across the microfluidic channels and/or vessels 2060 in the scaffold block 2050 and a corresponding increase in fluid flow rate across the pressure jumper 2030. As part of a negative feedback loop, in response to a decrease (or an increase) in fluid flow rate across the pressure jumper 2030, the system 1000 can stimulate a pump 1020 to increase (or decrease) the amount of fluid in the system 1000 and/or the rate of flow to result in a constant pressure, shear stress, and/or flow rate across the microfluidic channels and/or vessels 2060 in the scaffold block 2050. In this way, by measuring flow rate across the pressure jumper 2030, the amount of angiogenesis or vessel loss can be monitored in real-time and fluid flow can be controlled to maintain the microphysiological model.

The resistance (or pressure) across the microfluidic channels and/or vessels 2060 in the scaffold block 2050 can also decrease or increase, due to vessel dilation or constriction, respectively. The resistance (or pressure) across the microfluidic channels and/or vessels 2060 in the scaffold block 2050 can decrease as the result of vessels becoming larger, or vasodilation. This increases the amount of fluid volume of the microfluidic channels and/or vessels 2060 in scaffold block 2050 and results in a decrease in fluid flow rate across the pressure jumper 2030. Conversely, if the vessels become smaller, also known as vasoconstriction, then the fluid volume of the microfluidic channels and/or vessels 2060 in scaffold block 2050 can decrease, which can lead to an increase in the resistance (or pressure) across the microfluidic channels and/or vessels 2060 in the scaffold block 2050 and a corresponding increase in fluid flow rate across the pressure jumper 2030. As part of a negative feedback loop, in response to a decrease (or an increase) in fluid flow rate across the pressure jumper 2030, the system 1000 can stimulate a pump 1020 to increase (or decrease) the amount of fluid in the system 1000 and/or the rate of flow to result in a constant pressure, shear stress, and/or flow rate across the microfluidic channels and/or vessels 2060 in the scaffold block 2050. In this way, by measuring flow rate across the pressure jumper 2030, vasodilation or vasoconstriction can be monitored in real-time and fluid flow can be controlled to maintain the microphysiological model. Other biological phenomena can be monitored via the system 100. While it is theoretically possible to determine some phenomena that are occurring via the sensor 2040, it is also be within the scope of this system 1000 to be able to access fluid reservoir 1010 for chemical and biological marker measurement. This can be used as more data for the computer of the system 1000.

The system 1000 can be configured to monitor multiple parameters and/or biologic phenomena, via a sensor 2040, and/or fluid reservoir 1010, such that a computer can determine whether specific biological phenomena are occurring within the manifold device 2000. Biological phenomena that system 1000 can monitor includes, but is not limited to, angiogenesis, neoangiogenesis, anastomosis, vasculogenesis, vascular tone, tortuosity, vasodilation, vasoconstriction, malnutrition, normoxia, hypoxia, hyperoxia, hypotension, hypertension and combinations thereof. The computer can use software and/or machine learning to develop a readout for biological phenomena. The fluid reservoir 1010 can be accessed manually, or further connected to instrumentation that can measure chemical and/or biological parameters. Determining whether sensor data patterns are due to angiogenesis or vasodilation (or other biologic phenomena) can be executed via software. The software can be configured to look at the rate of change of the flow rate data. Software can also be configured to create virtual models of either or both phenomena happening at once and use machine learning to predict and/or output that information.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Monitoring and Controlling Perfusion in Vascularized Microphysiological Models Using an Instrumented Microfluidic Manifold Device Microphysiological models have the potential to eliminate the use of animals for pharmaceutical testing, immune response, and disease modeling. However, most microphysiological models, also known as organ-on-chip devices, lack the necessary vasculature needed to correctly recapitulate organ systems in vitro. Blood vessels play a vital role in organ function and must be included if questions about physiological phenomena of the biology, chemistry, and physics of these organs are to be addressed. Moreover, control of the vascularized microphysiological model is paramount to the success of these devices in the clinic. Here, we introduce a platform technology that integrates vasculature in 3D microphysiological model systems to control and monitor perfusion in real-time. Our platform can support different vascularized tissues, which can be used to enhance drug screening, explore fundamental biology, understand diseases, and help reduce the use of animals in pharmaceutical and commercial product testing.

Introduction

A microphysiological model, or MPM, is a microfluidic based system that integrates physiological phenomena into an engineered platform. Using MPMs researchers can study myriad questions about the incorporated biology, chemistry, and physics. The ultimate goal of microphysiological model research is to recapitulate the fundamental function of human organs outside the body. Scientists can use these synthetic organ systems for drug toxicity screenings, immune response studies, and disease modeling. Animal models are the gold standard for investigating physiological systems because they give "big picture" results of entire organ function, are handled easily and reliably, and have been shown to be associated with human outcomes. However, the results obtained from animal models can fail to correlate with human trials mostly due to cell genotype and phenotype differences, which lead to problems later in the investigation cycle (especially for drug testing). MPM systems alleviate the problems associated with animal models because they offer a solution that uses human tissues, eliminating the need to guess how a human organ would respond to stimuli. The most popular human tissues being studied for MPMs right now are the lung, liver, kidney, heart, and brain. These organs are often targeted because they have a high impact on the outcomes of toxicity and immune response testing. By creating organ systems via microfluidics, researchers have another tool to study the underlying physiological phenomena necessary for understanding the human body. MPM research is full of potential for understanding human diseases and advancing cell therapies and drug treatments to fight diseases.

A major challenge for microphysiological model research is incorporating vasculature into the engineered tissues, [1] Vasculature is found in every major organ in human body. Blood vessels are responsible for supplying nutrients to cells and tissues, as well as transporting waste created by those organs. Without vasculature, these processes are limited by diffusion which is not sufficient for large 3D organs. Most MPMs consist of very small tissue constructs, often in 2D, with one or two cell types specific to the organ of interest. These systems fail to address the need for dynamic, vascularized tissue constructs with realistic geometries, flow rates, and supporting cell types. Endothelial cells make up the lining of blood vessels and play a critical role in the function of vascularized tissues. Endothelial cells form close connections with neighboring cells via tight junctions which control the passage of nutrients and waste to and from the tissue. Without a vasculature network in the modeled tissue, the full physiological picture is missing for the organ system. Researchers have started to address the need for vasculature in tissues by developing standalone blood vessels on a microfluidic MPM platform. There are two strategies for creating blood vessels in vitro: directed formation and spontaneous formation. Directed formation is when vessels are created using predefined scaffold geometries. Examples of this are found here. [2-6] Directed formation allows for precisely patterned vascular networks to be created with total fluid control within the system. Control over the fluid dynamics is incredibly valuable when trying to manipulate the tissue and engineer it a certain way. However, with directed formation it is difficult to create vessels much smaller than 100 μm in diameter due to physical limitations of fabrication techniques, and the seeding the vessels with cells consumes a lot of reagents and materials, which can drive up monetary expenses and time related costs. Spontaneous formation on the other hand is when vessels are created randomly in a scaffold via angiogenesis, the phenomena by which vessels proliferate and branch off to form a greater vasculature network. Examples of this can be found here. [7-11] Angiogenesis occurring in vitro suggests that embedded endothelial cells are behaving as they would in the body, a key feature when recapitulating any organ system. The limiting factor of a system relying on spontaneous vessel formation is the inability to precisely control fluid moving through formed vessels. Manipulating the fluid dynamics of a synthetic tissue is valuable in microphysiological model research, because it allows the researcher to ask specific questions related to how cells depend on fluid transport biologically, chemically, and physically. It is well known that endothelial cells will polarize along flow direction in vivo, which occurs due to shear stress acting on the cell via moving blood or lymph. These cells will also undergo genetic and molecular changes due to this shear stress, upregulating various genes and secreting different signals and biomarkers. Consequently, engineered synthetic tissues require proper vascularization to recapitulate true physiological response. Without control over the fluid dynamics within a system, these phenomena cannot occur. For example, the lung-on-chip created by Ingber et al. has a monolayer of epithelial cells separated from a monolayer of lung alveolar cells via a synthetic membrane. There is no incorporation of blood vessels in this system, but vessels exist in the lung in vivo and support the basic function of the lungs.

Since most MPM devices lack critical vasculature, the results gleaned from synthetic tissue systems are incomplete, Microphysiological models that are created today are mostly one-off creations of the basic functional unit of the organ of interest. This "artisanal" nature of MPM production makes it difficult to get reproducible results from the nth copy of a single MPM system and it is highly unlikely that different MPM systems, out of different labs or companies, can be compared to each other. This represents a critical gap in the manufacturing of MPM systems. Reproducibility is important because if an MPM system has any hope of making it through a clinical trial; the results from the nth system need to be just as reliable as the first. The way MPMs become reliable is through quality assurance and quality control. Currently, microphysiological models are validated for quality assurance via end point assays and analyses. This is not good enough as it requires sacrificing the experiment to determine its validity. Non-invasive methods for monitoring the quality of the organ system must be developed for future use in clinical trials. Moreover, controlling the quality of MPM systems will go towards the mass-production of synthetic tissues. Quality control is paramount in any manufacturing process, and the production of microphysiological models is no different. Towards quality assurance and control of organ systems, many avenues exist from biotechnology and engineering; from biomarker validation and cell genotyping, to flow sensing and impedance monitoring, these techniques can help assure and control the quality of a microphysiological model system, Described is an instrumented microfluidic manifold device for monitoring and controlling perfusion of vascularized microphysiological model devices. Controlled perfusion of the synthetic tissue via the device design and monitoring of perfusion in real time using a flow sensor instrument connected to the device was achieved. Computation fluid dynamics simulations were used to aid in the device design and developed mathematical equations that describe the fluid dynamics of our system. A manifold device was developed to incorporate multiple vessels within a synthetic tissue at once and to create relatively large scale tissue constructs. The flow sensor instrument connected to the device provides data to a negative feedback loop that adjusts manifold vessel flow for optimal shear stress and pressure. The platform can theoretically, given exceptional flow sensor resolution, quantify angiogenesis in real time via pressure drop within the manifold.

Experimental

Materials: Negative SU-8 2150 was obtained from Micro-Chem. Glass wafers 100 mm in diameter were obtained from University Wafer. Polydimethylsiloxane (PDMS) was obtained from Dow Corning as product Sylgard 184. The SLI-1000 flow sensor was purchased from Sensirion Inc. Tygon tubing was obtained from McMaster Carr. The Ismatec REGLO Digital 4-channel 8-roller peristaltic pump was purchased from ColeParmer.

Simulations: COMSOL Multiphysics was used to perform computational fluid dynamics simulations of the microfluidic manifold device. The device reservoir spaces were modeled as rectangular prisms with dimensions of 2 mm width, 3 mm height, and 26 mm length. The vessels were modeled as cylinders with a diameter of 500 µm and a length of 13 mm. The pressure jumper was modeled as a curved cylinder (semi-torus), with a diameter of 1000 µm and a length of 31.4 mm. The fluid density and viscosity were set at 1000 kg·m$^{-3}$ and 0.001 Pa·s, respectively. The inlet was modeled as a standard mass flow rate of 1000 µL·min$^{-1}$. The outlet was modeled as a pressure being open to the atmosphere (true in our system since it feeds to an off-chip reservoir equilibrated with ambient environment). A physics controlled mesh, on "Finer" setting, was applied to the model. Pressure and velocity heat maps were generated as a result, along with line graphs at various positions on the model. Simulations of anastomosis were carried out using the same parameters except adding more vessels at varying angles connected to the original vessels without connecting to the reservoirs or jumper.

Device Fabrication: The microfluidic manifold device was fabricated via replica molding of PDMS from a patterned master mold. The master molds were fabricated via photolithography. Negative SU-8 2150 photoresist was spin-coated on a cleaned and plasma treated glass wafer at 500 rpm for 10 sec, followed by 1250 rpm for 30 sec to achieve a thickness of approximately 500 µm. The wafer was then soft baked on a hot plate at 65° C. for 10 min, then at 95° C. for 120 min, and finally at 65° C. for 10 min. The SU-8 on the wafer was exposed to a total dose of 1260 mJ cm$^{-2}$ ultraviolet light via a custom designed film mask over 130 sec. After exposing the wafers, the SU-8 was baked at 65° C. for 5 min, then at 95° C. for 30 min, and finally at 65° C. for 2 min. The SU-8 was then developed to wash away the unexposed photoresist for 30 min. The wafers were then hard baked at 150° C. for 60 min before replica molding. Device replicas were cast from the master molds using PDMS at a 10:1 elastomer to curing agent ratio, cured at 100° C. for 20 min, then bonded to a glass slide via oxygen plasma. An Ismatec peristaltic pump was used to create a closed loop of fluid from an off-chip reservoir to the device and back. A Sensirion SLI-1000 flow rate sensor was connected in-line to a Tygon tubing pressure jumper.

Device Operation: Tubing for the inlet, outlet, and two pre-sensor tubing segments were inserted directly into the PDMS devices. This tubing is connected to a peristaltic pump to drive fluid to the device. To prime the device, reservoirs were filled simultaneously, via two separate channels on one pump, to ensure continuity of fluid. The mathematical theory of the parallel branches having the same pressure drop only holds true if the fluid is continuous. Once the reservoirs are filled, the pumping was halted so that the outlet can be disconnected from the pump to achieve the proper pressure drop and fluid movement direction. The outlet is instead directed into the media reservoir that supplies the inlet with fluid. The two pre-sensor segments were each connected to one end of the flow sensor. The peristaltic pumping was then resumed to establish the flow loop within the device and sensor. The total inlet flow for all devices was set to 1000 µL min$^{-1}$. After allowing the fluid flow to stabilize, flow rate measurements were recorded for a period of 1 min. This ensures an accurate and averaged flow rate measurement for comparison to other devices.

Results & Discussion

Device Design. A manifold is a reservoir that branches into separate smaller openings. A microfluidic manifold device to have branching "vessel" flow was designed. Many branches are needed because we want to be able to create relatively large tissue constructs for future experiments, approximately 1 cm$^3$ in volume, and ensure that the entire tissue could be vascularized and sustained. Large tissue constructs help bridge the gap between small scale in vitro testing and human-scale in vivo studies. FIGS. 1A-1E show a schematic of the manifold device design. An inlet reservoir branches out into eight channels and one pressure jumper. All branches are reconnected to the outlet reservoir for pooling of fluid at the outlet. Due to the way fluid is introduced into the manifold, explained further in the Mathematical Modeling section, a pressure drop is established between the inlet reservoir and outlet reservoir that drives fluid through the branching channels. By connecting a flow sensor to the pressure jumper, flow rate within the jumper is correlated to the pressure drop down the branches. Over time as the vessels in the tissue undergo angiogenesis, and anastomose, the tissue scaffold resistance will decrease leading to a decrease in the flow rate through the jumper. This phenomenon is shown in FIGS. 1A-1E.

Mathematical Modeling. Starting from the Navier-Stokes equations for fluid flow in cylindrical coordinates, the dynamics of the system was modeled mathematically. Assuming steady state, fully developed, laminar flow of an incompressible fluid, the Navier-Stokes equations reduce to one equation where the fluid velocity, u, in the z-direction only depends on the radial r-dimension of the cylinder and pressure, $$\frac{1}{r}\frac{\partial}{\partial r}\left(r\frac{\partial u_z}{\partial r}\right) = \frac{1}{\mu}\frac{\partial P}{\partial z},$$

where µ is the dynamic viscosity of the fluid. Given the boundary conditions:

$$\begin{cases} u_z(r) = 0, & r = R \\ \dfrac{\partial u_z}{\partial r} = 0, & r = 0 \end{cases},$$

where R is the radius of the cylinder and solving the Navier-Stokes equation gives $$u_z(r) = \frac{-1}{4\mu}\frac{\partial P}{\partial z}\left(R^2 - r^2\right) = u_{max}\left(1 - \frac{r^2}{R^2}\right).$$

Assuming pressure decreases linearly then, $$-\frac{\partial P}{\partial z} = \frac{\Delta P}{L},$$

where $\Delta P$ is the pressure drop through the cylinder and L is the length of the cylinder. Integrating the velocity over the r-dimension and $\theta$-dimension gives flow rate, $Q=\int_0^{2\pi}\int_0^r u_z(r)r\ dr\ d\theta$. Solving this equation yields $$Q = \frac{\pi R^4}{8\mu}\frac{\Delta P}{L} = \frac{u_{max}}{2}\pi R^2.$$

Rearranging this equation and subbing in hydrodynamic resistance, $$R_h = \frac{8\mu L}{\pi R^4},$$

gives, $\Delta P=QR_h$, which is the fluid dynamics equivalent of Ohm's Law. This is the fundamental concept behind our design. Parallel resistors in a circuit have the same voltage drop, therefore, parallel branching conduits connected to an inlet and outlet reservoir will all have the same pressure drop.

In the system, assuming the hydrodynamic resistance of the inlet and outlet reservoirs are orders of magnitude smaller than the hydrodynamic resistance of the pressure jumper, the total hydrodynamic resistance can be calculated by, $$\frac{1}{R_h} = \frac{1}{R_j} + \sum_{v=0}^{N_v}\frac{1}{R_v},$$

where $R_j$ is the hydrodynamic resistance of the pressure jumper, $N_v$ is the number of vessels in the scaffold, and $R_v$ is the hydrodynamic resistance of a vessel. This equation can be simplified to $$R_h = \frac{1}{\left(\frac{1}{R_j} + \frac{1}{R_s}\right)},$$

where the hydrodynamic resistance of the scaffold is $$R_s = \frac{1}{\sum_{v=0}^{N_v}\frac{1}{R_v}}.$$

This simplification allows for the scaffold to be treated as a sum of the parallel resistances of the vessels within it. For example, if all the vessels have the same resistance then this reduces to $$R_s = \frac{R_v}{N_v}.$$

Supplying this system with a set total flow rate, $Q_{tot}$, allows for a new equation for pressure drop, $$\Delta P = \frac{Q_{tot}}{\left(\frac{1}{R_j} + \frac{1}{R_s}\right)}.$$

As the predefined vessels proliferate and anastomose, $N_v$ increases which means $R_s$ decreases, leading to the pressure drop in the system decreasing with it. The pressure drop can be detected via a decrease in flow rate in the jumper since the jumper's resistance will not change but the pressure will. The measured decrease in flow rate is used as feedback to adjust the total inlet flow rate for the whole device. This negative feedback of perfusion can be correlated to total vascularization and allows for maintenance of optimal perfusion pressures.

One way to maintain optimal perfusion pressures is to target a desired shear stress in the vessels. Since the velocity is only in the z-direction and depends on the radial r-dimension, the only shear stress in the cylinder is $$\tau_{rz} = \mu\left(\frac{\partial u_r}{\partial z} + \frac{\partial u_z}{\partial r}\right),$$

which further reduces to $$\tau = \mu\frac{\partial u_z}{\partial r}.$$

Solving this equation yields $$\tau = \frac{2\mu u_{max}r}{R^2},$$

where R is the radius of the cylinder. The maximum shear stress occurs at r=R, therefore, $$\tau_{max} = \frac{2\mu u_{max}}{R} = \frac{R}{2}\frac{\Delta P}{L}.$$

By choosing an optimal value of $\tau_{max}$ for a vessel with known R and L, the optimal $\Delta P$ can be calculated. As the pressure drops in the system due to increasing number of vessels (decreasing resistance), the maximum shear stress in the source/parent vessels will also decrease. To maintain a constant pressure drop and maximum shear stress while the resistance decreases, the flow rate needs to increase. Therefore, by increasing the total flow rate through the system as the number of vessels increases, the pressure drop can be held constant. The optimal pressure facilitates shear stress at the blood vessel walls, keeping blood vessels patent.

Figure 2:
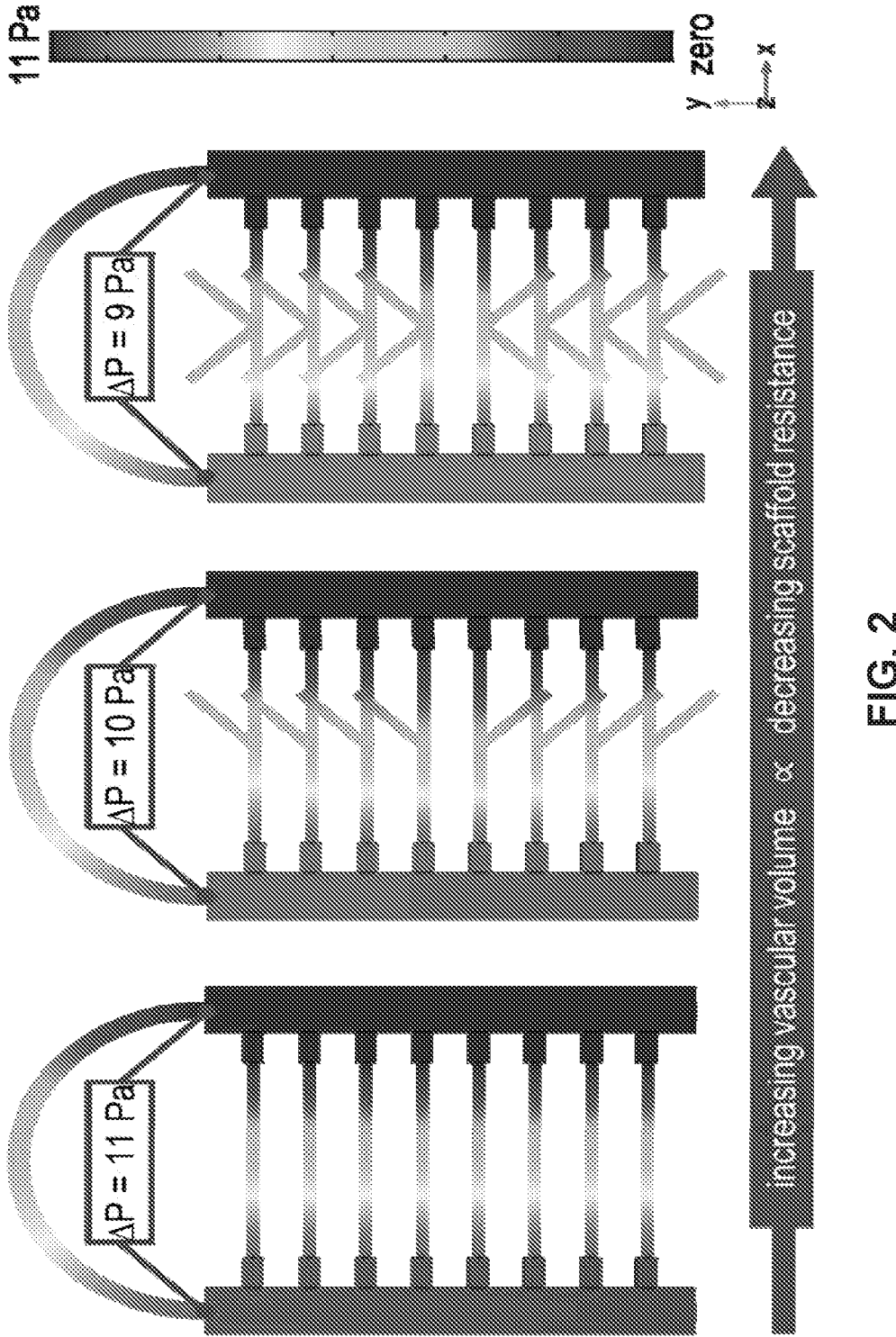
FIG. 2 shows COMSOL Multiphysics computational fluid dynamics simulation results.
Figure 3A:
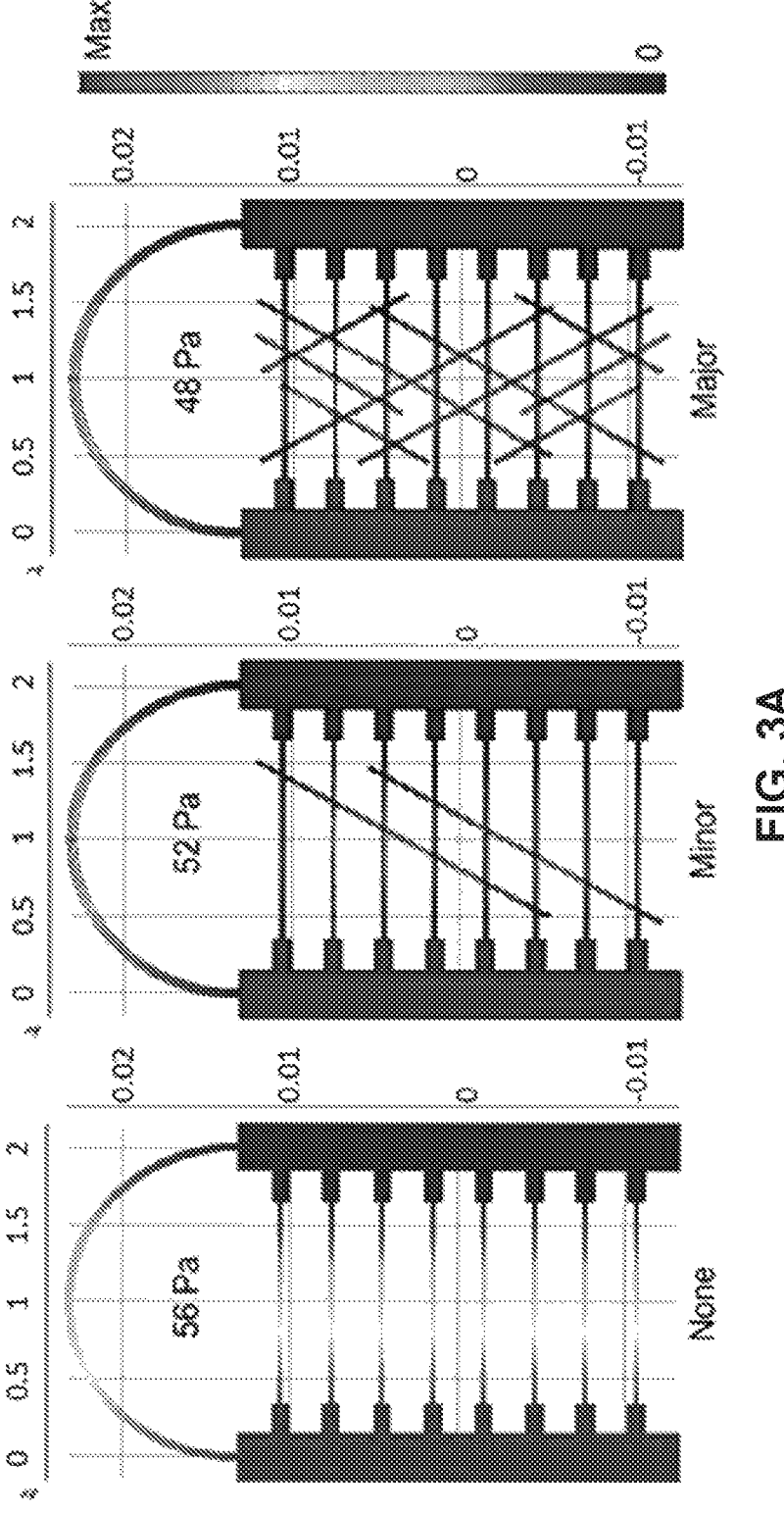
FIGS. 3A-3C show simulations of anastomosis of vessels. As angiogenesis occurs, pressure in the system goes down leading to decreased velocity and flow rate in the pressure jumper where the flow sensor can measure it.
Figure 3B:
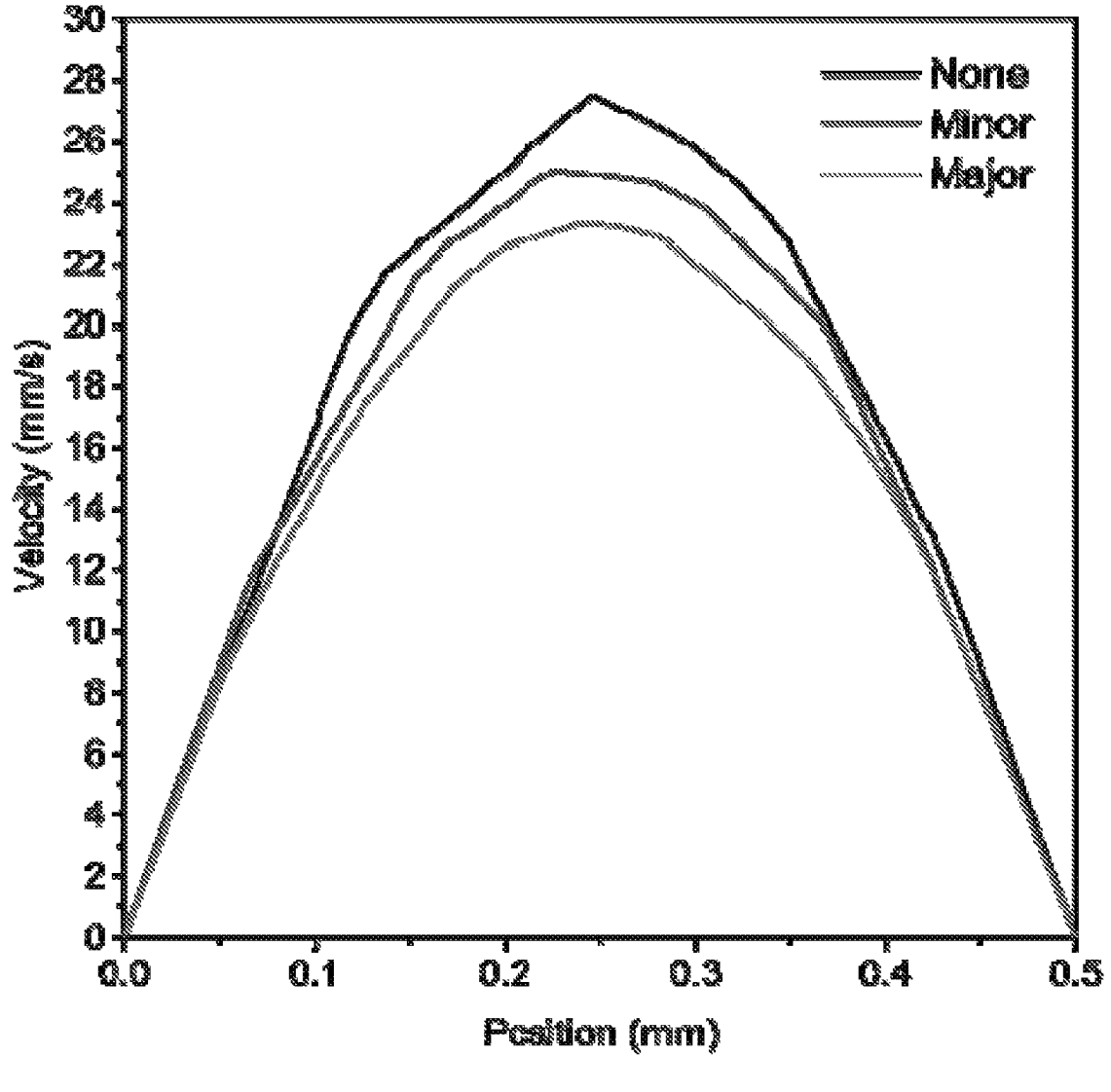
Figure 3C:
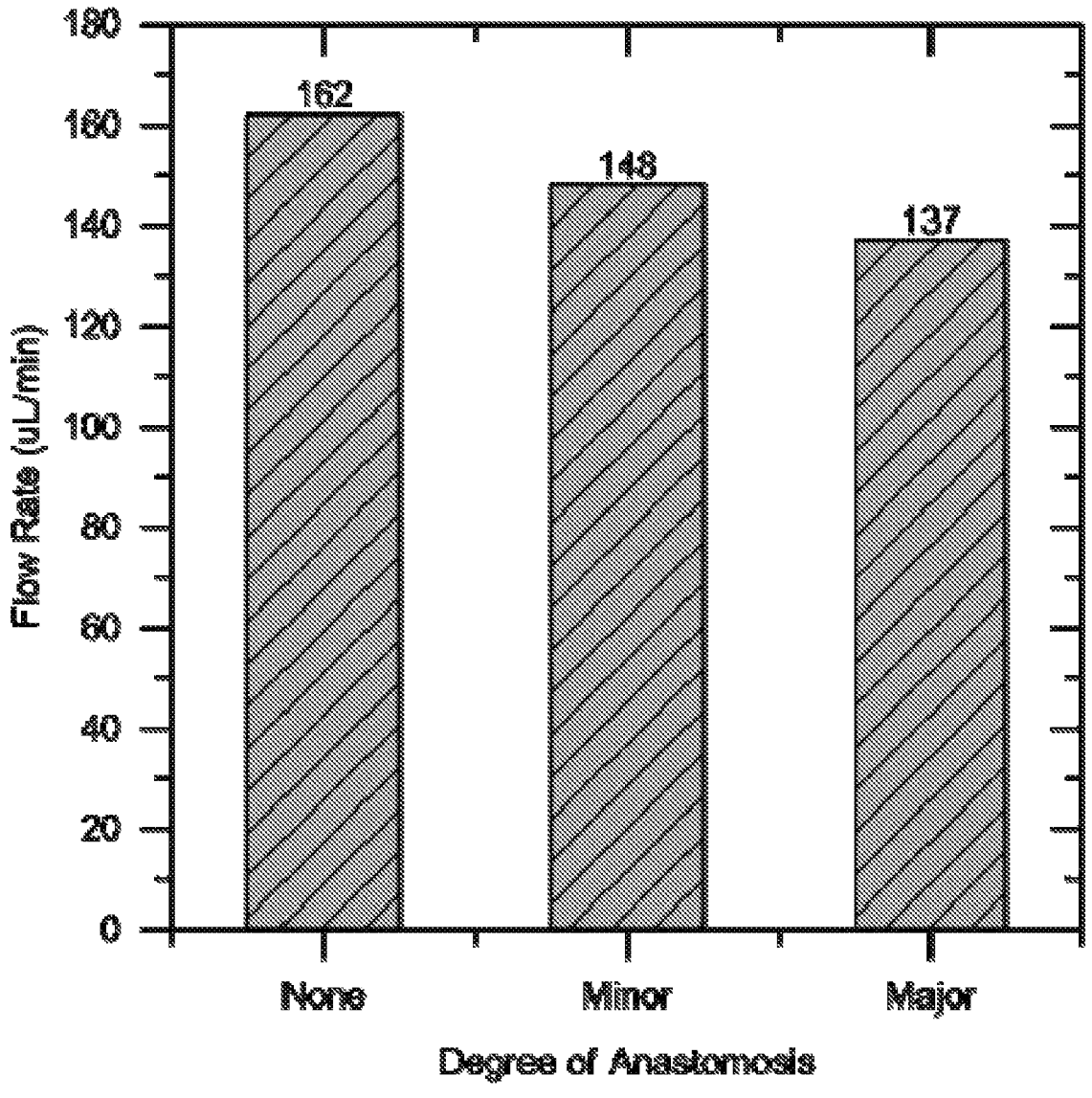

Simulations. Computational fluid dynamics simulations were performed to simulate the microfluidic manifold device. To validate the manifold device design, a simulation was performed with a given inlet flow rate to generate a specific shear stress and pressure drop across the branches. FIG. 2 shows the result of this simulation. The first heat map displays the pressure in the system. The inlet reservoir is at a higher pressure than the outlet reservoir, creating a pressure gradient in the branches. The red cut line is used to quantify the pressure in the branches shown in the line graph. This pressure drop drives fluid through the branches, as shown in the second heat map of velocity. The maximum fluid velocity in the pressure jumper is higher than the maximum velocity in the branches because the hydrodynamic resistance in the pressure jumper is lower than that of the branches. The red cut line is used to quantify the velocity in the cross section of the branches shown in the line graph. The line graph shows that the maximum velocity occurs at the center of every branch and that every branch has the same velocity, which is correct when all the branches have the same hydrodynamic resistance. Slight differences in the maximum velocity can be attributed to mesh differences per branch used to solve the COMSOL model.

The second simulation also models the manifold at steady state, except with varying degrees of vessel angiogenesis and anastomosis, as shown in FIG. 2. The sprouting and connecting of vessels is represented here as happening to a minor or major degree arbitrarily within the scaffold. The heat maps of pressure are normalized to maximum pressure within the given system, so although the heat maps look very similar, the maximum pressure in each system decreases as the degree of anastomosis increases. This phenomenon is shown in FIG. 2 as decreasing from 11 Pa with no anastomosis to 10 Pa with eight branches to 9 Pa with sixteen branches. The velocity profile in the cross section of the pressure jumper is plotted in the next graph, showing the decrease in velocity due to decreasing pressure drop. The flow rate calculated corresponds to this velocity for the given pressure jumper and is plotted in the bar graph, showing a decreasing flow rate detectable by the flow rate sensor at different degrees of anastomosis.

Figure 8:
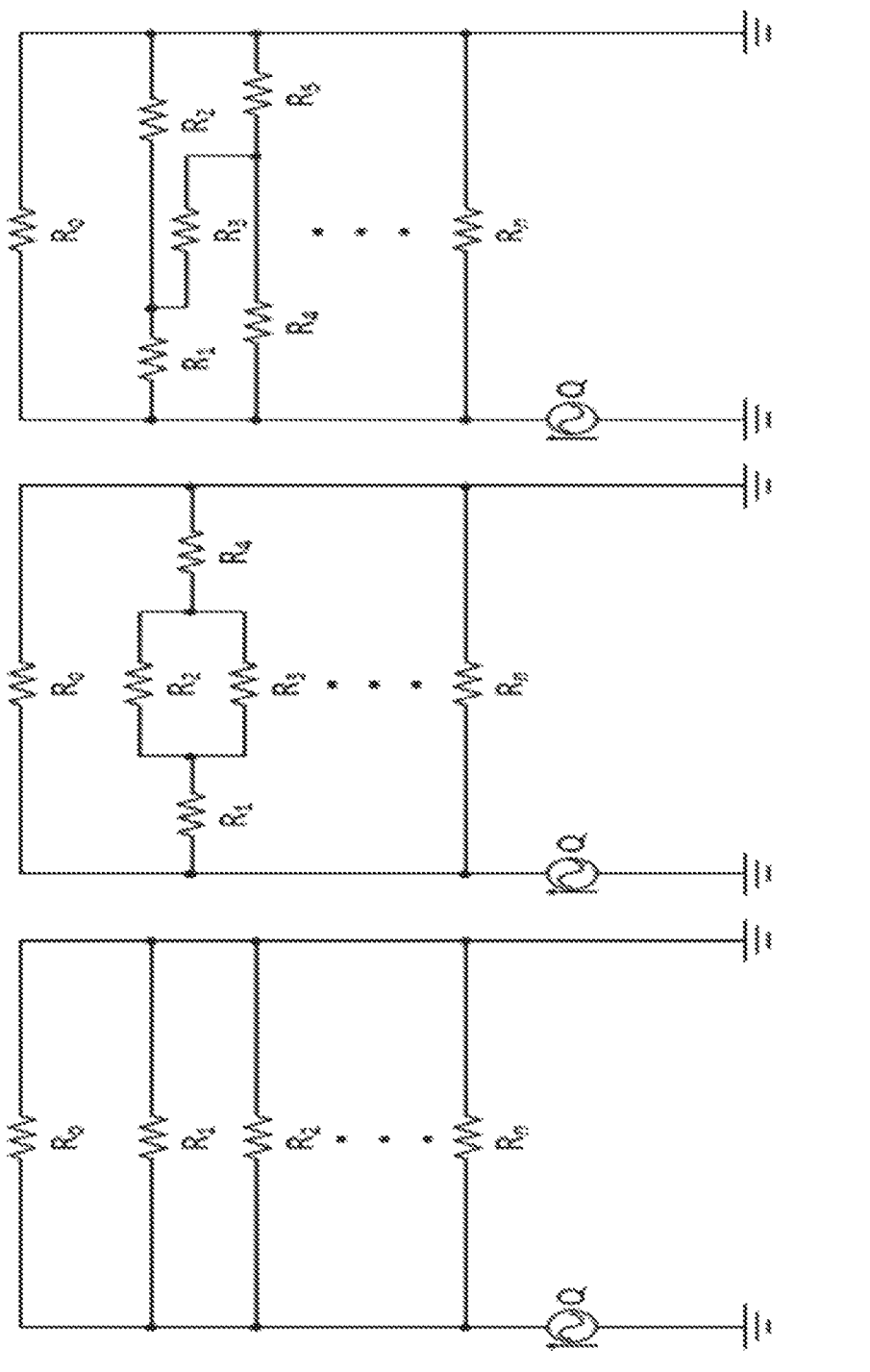
FIG. 8 shows circuit diagrams of equivalent vascularized scaffold networks. Flow rate, Q, is supplied by a peristaltic pump and directed through Ro, which is always the pressure jumper, and the remaining R1 to Rn. Three different configurations are shown: 1) basic parallels, 2) parallels that each split into multiple new vessels, and 3) parallels that interconnect.
Figures 9A, 9B:
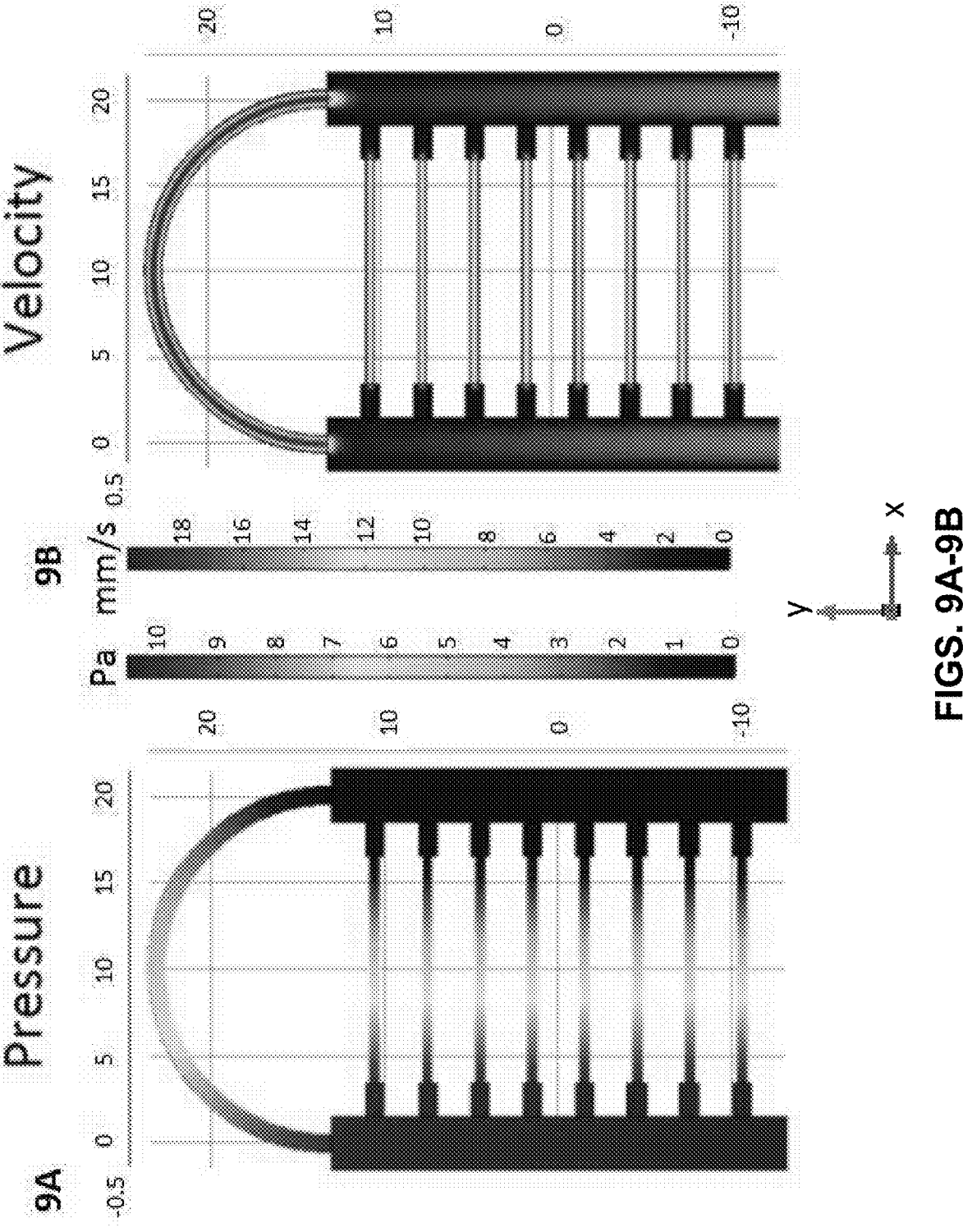
FIGS. 9A-9LL show heat maps from COMSOL which demonstrate the geometry that was simulated to evaluate the relationship between decreasing scaffold resistance (parallel conduits) and flow rate in the jumper (curved path).
Figures 9C, 9D, 9E, 9F, 9G, 9H:
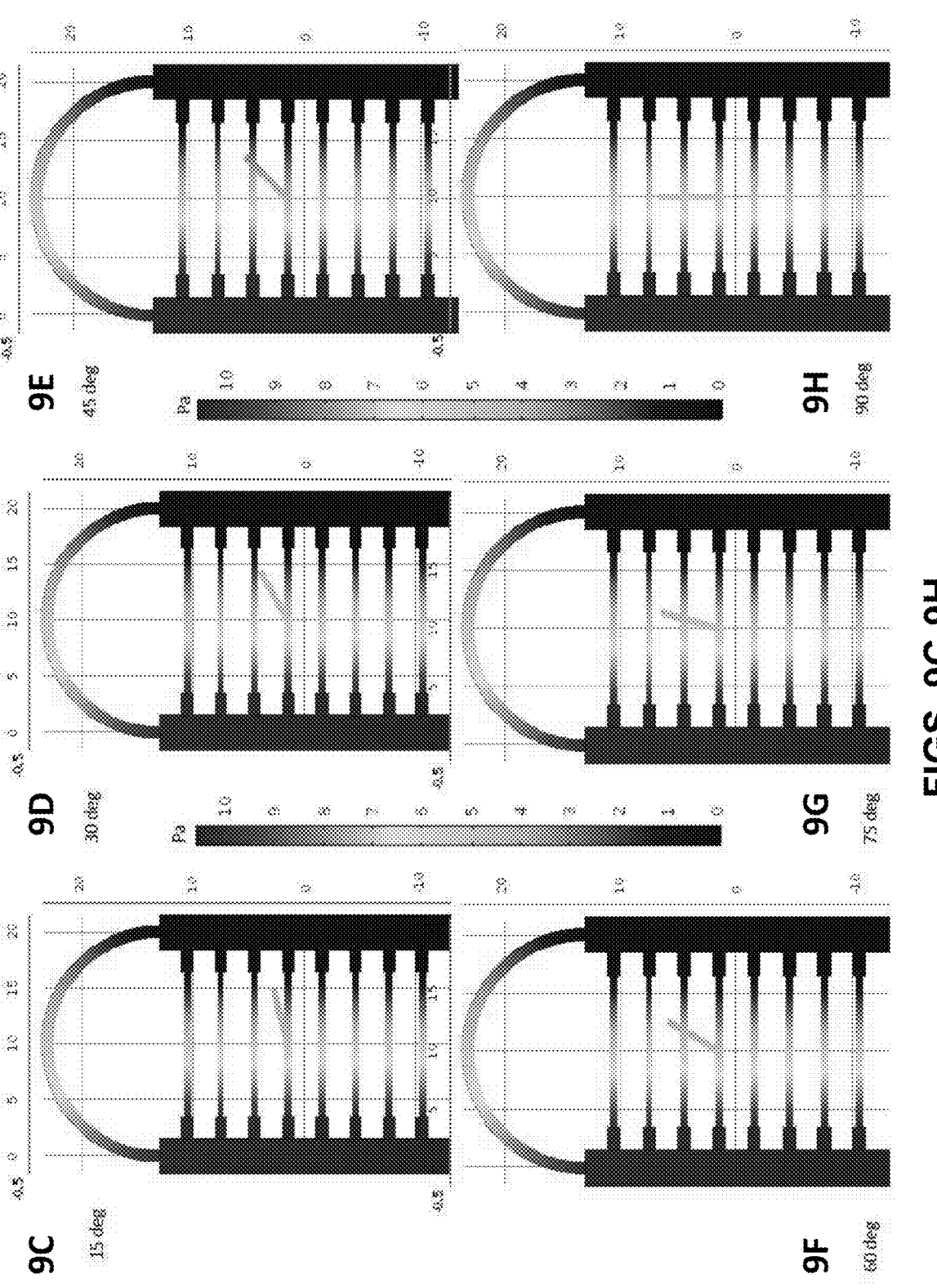
Figures 9I, 9J, 9K, 9L, 9M, 9N:
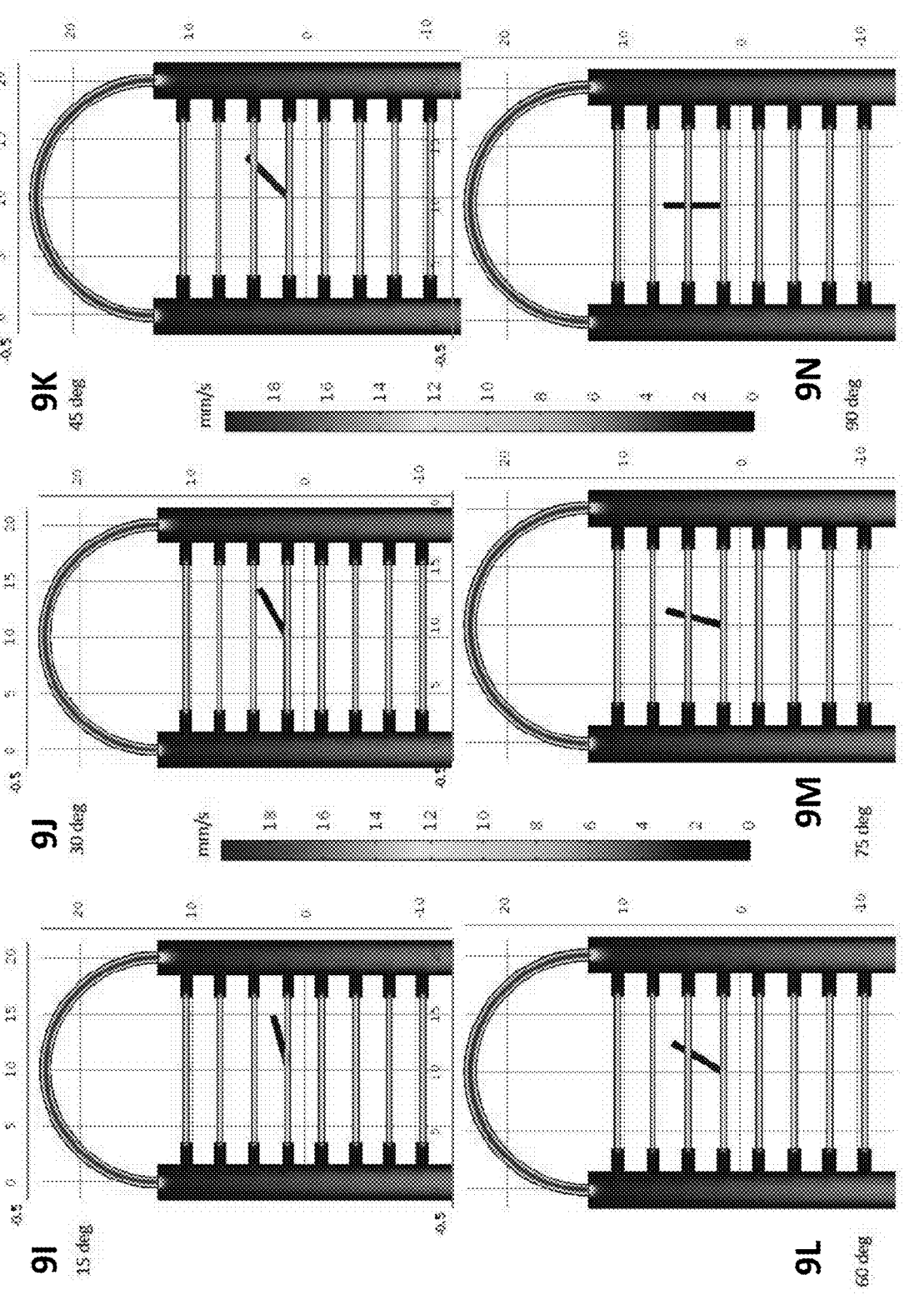
Figures 9O, 9P, 9Q, 9R, 9S, 9T:
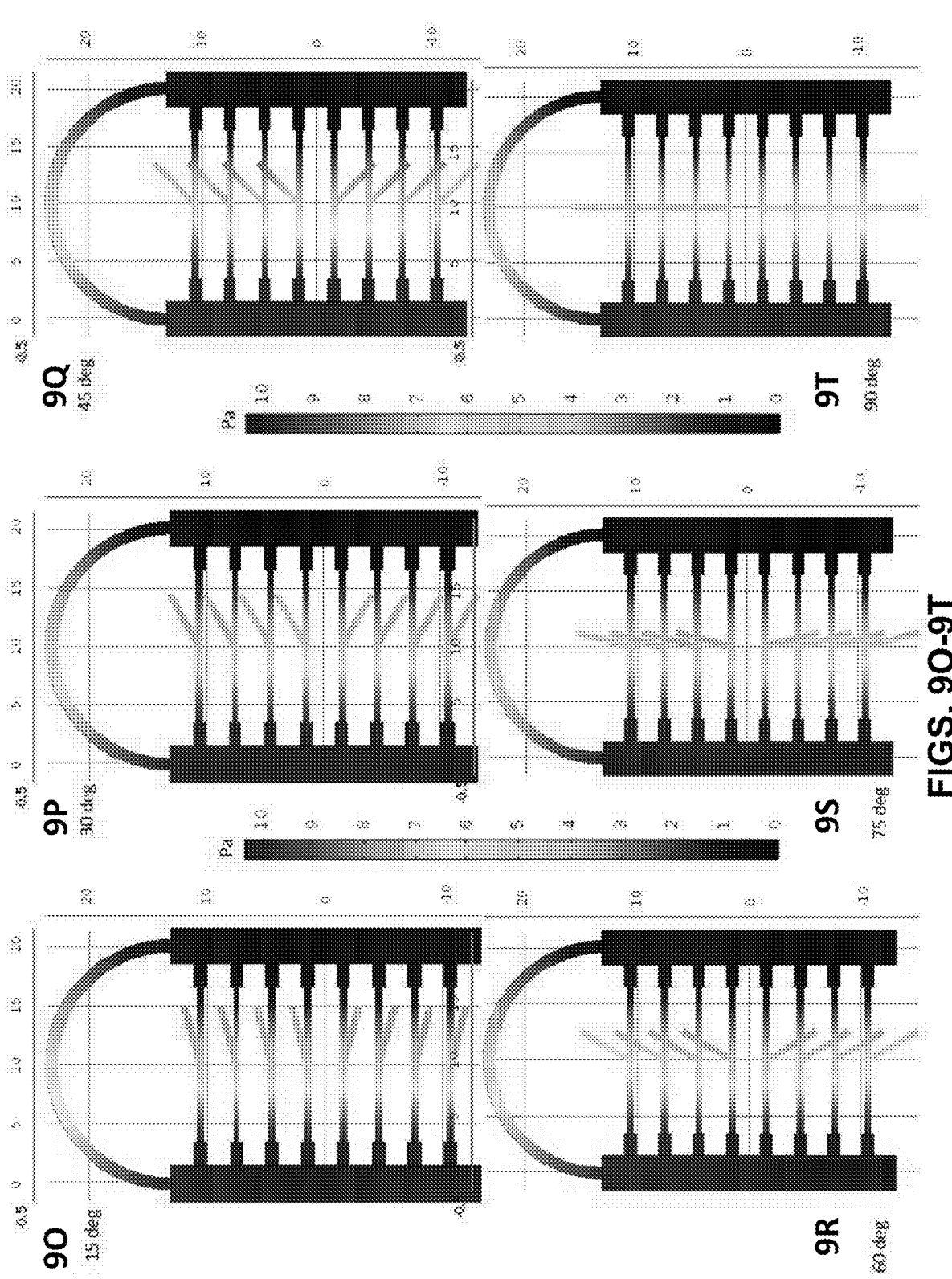
Figures 9U, 9V, 9W, 9X, 9Y, 9Z:
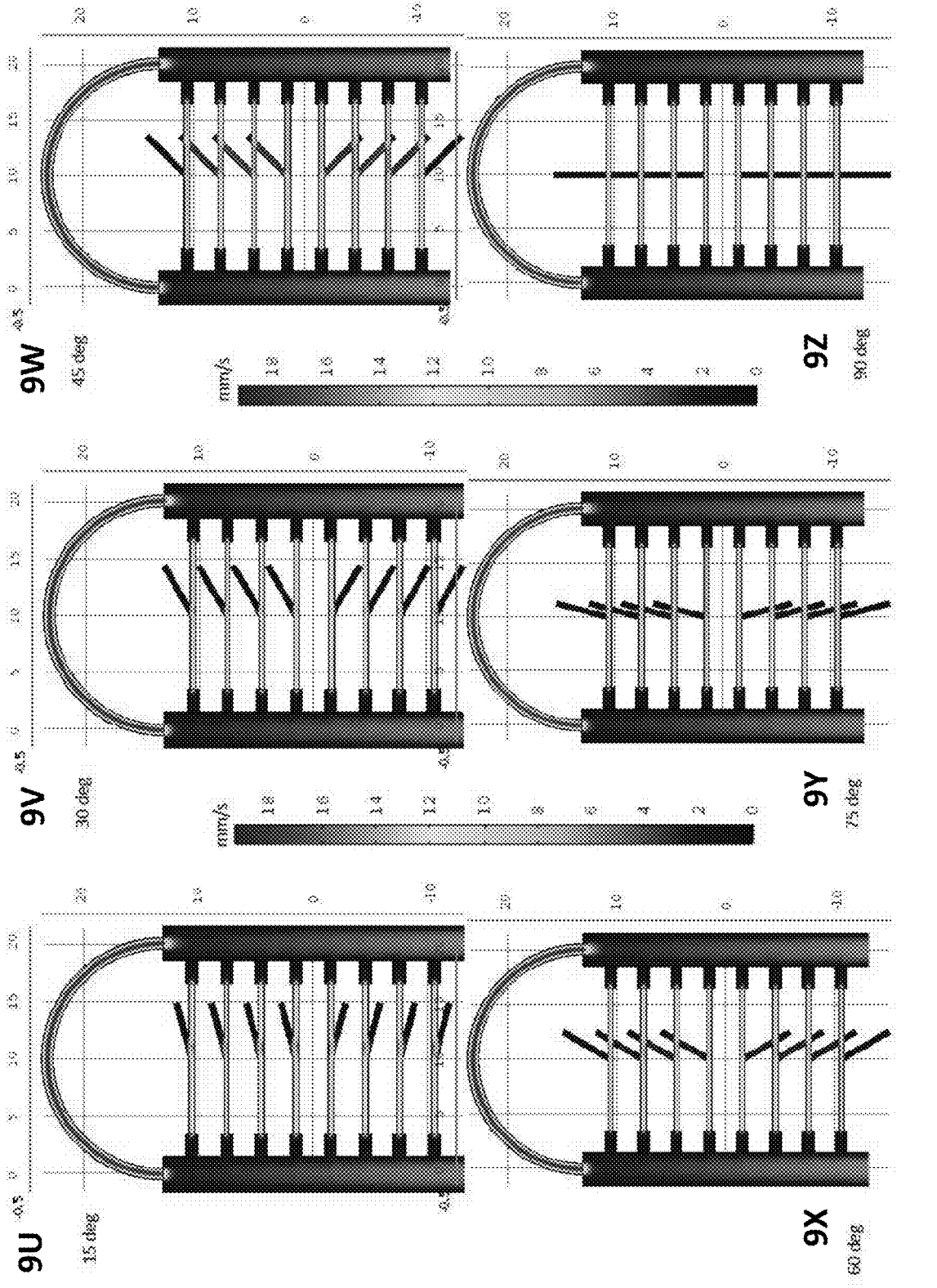
Figure 9A:
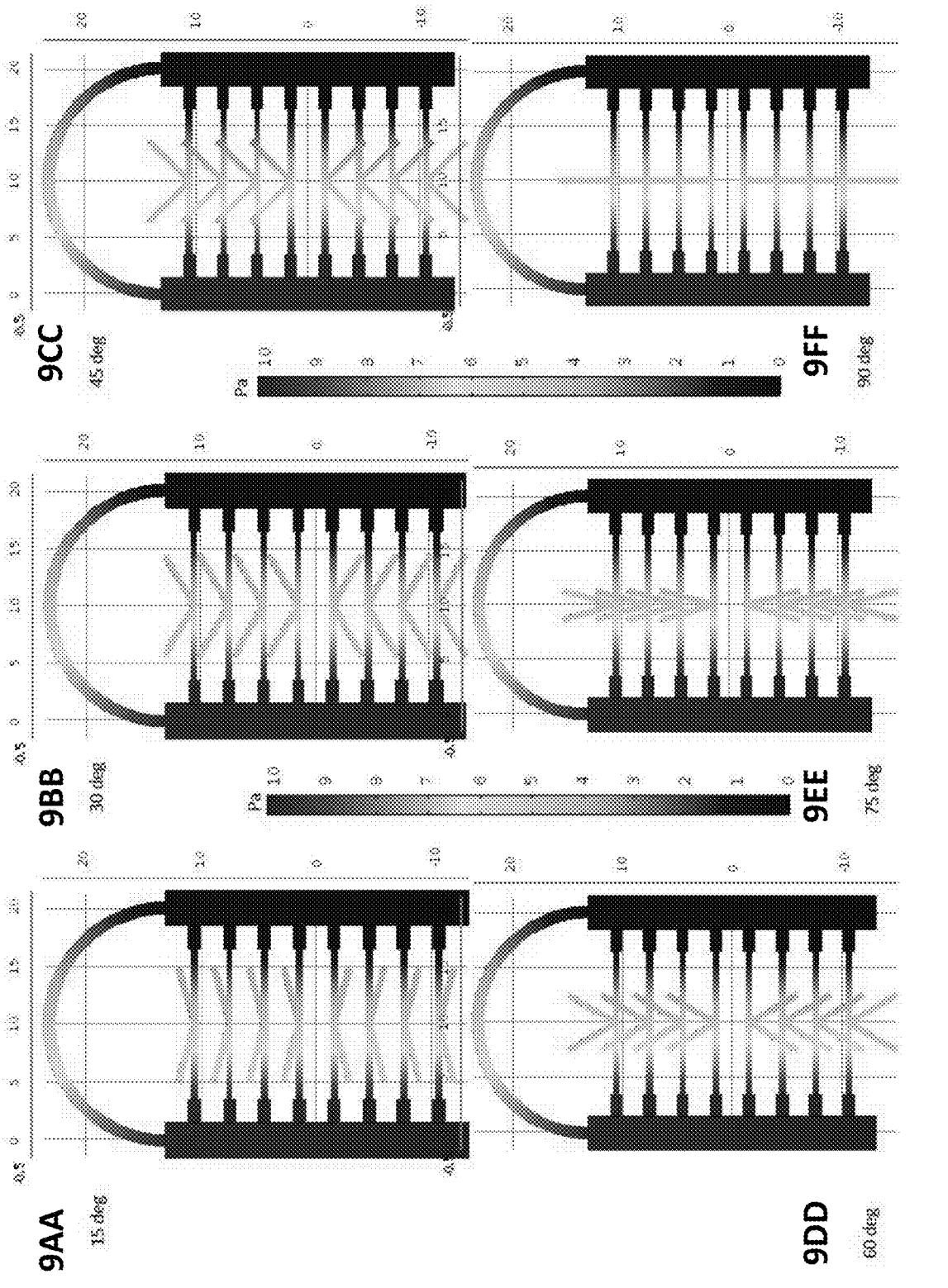
Figure 9G:
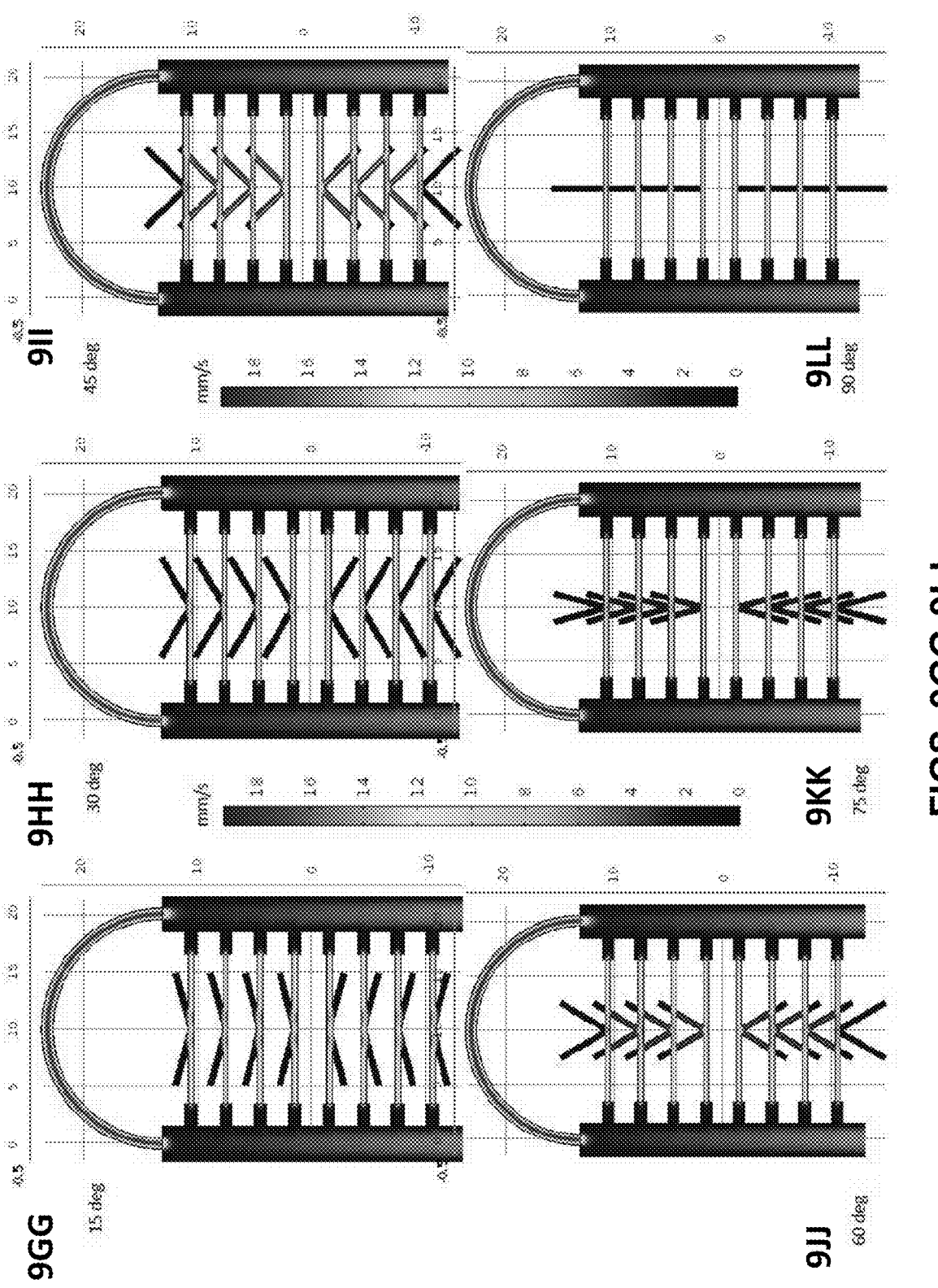

Circuit Model. A lumped element model of the manifold device was developed to analyze current and future iterations of the design. The entire manifold can be modeled as a constant current source connected to resistors in parallel. This assumes that the reservoirs of the manifold are modeled as wires with no resistance. FIG. 8 shows circuit diagrams of equivalent vascularized scaffold networks, Flow ate, Q, is supplied by a peristaltic pump and directed through Ro, which is always the pressure jumper, and the remaining R1 to Rn. Three different configurations are shown: 1) basic parallels, 2) parallels that each split into multiple new vessels, and 3) parallels that interconnect. Using nodal analysis the voltage at each node is calculated. Once each node has been solved for, the current through the "pressure jumper" resistor can be calculated for that given model. An example lumped element model of the original manifold contains nine resistors (one for the jumper, eight for the branches) and two nodes (including ground). Nodal analysis results in one equation with one unknown to solve for the voltage drop. For the model shown in FIG. 2 where six branches have a secondary branch connecting it to its neighbor, the circuit model consists of 27 resistors (since the connections effectively break up the original resistors into smaller resistors in series) and 14 nodes (including ground). Nodal analysis results in 13 equations with 13 unknowns, which are the voltages at each node. While this can be solved by hand, the number of equations and unknowns will quickly rise as more connections between the branches are made. Therefore, MATLAB was used to solve for the voltages in these circuits. This circuit model provides a means to analyze any pattern of manifold branching, without the need to simulate every possibility in COMSOL. Furthermore, this circuit model allows for a quick estimation of the sensor readout from any fabricated device.

Figure 7:
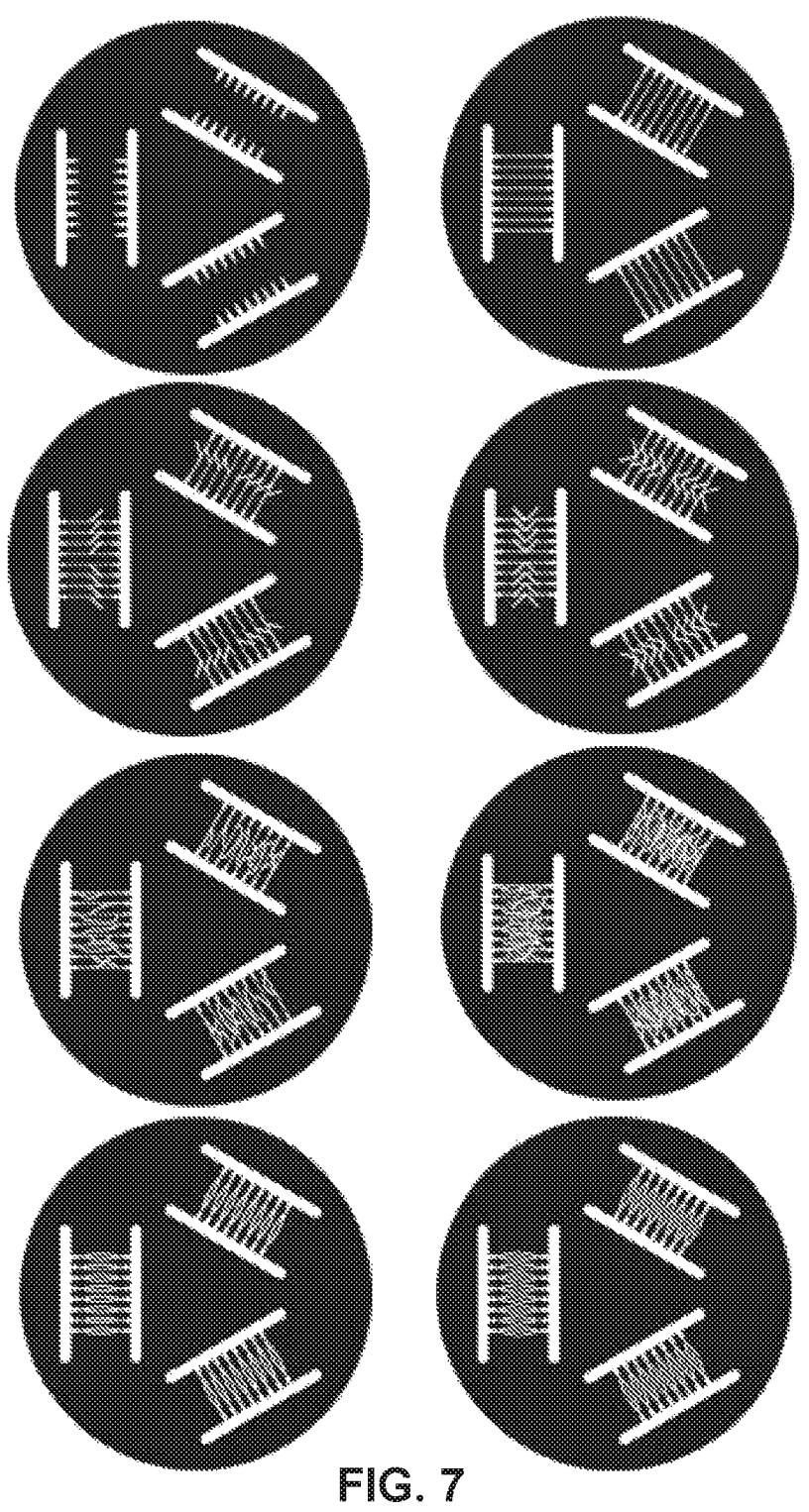
FIG. 7 shows photolithography mask designs. High resolution PDF's were sent to a printing company to print these masks on transparent Mylar film.

Device Fabrication. The masks were designed to pattern three devices per wafer in SU-8, while the pressure jumper was added to the device during operation. The original mask incorporates the inlet and outlet reservoirs with eight branches connecting them. Subsequent masks deviate from the original in two groups. The first group of masks is the parallel splitting group, where each branch splits in half once, then those splits each split in half, and finally a mask where each of these new splits also split in half. The second group of masks is the angiogenesis mimic group. Starting from the original device, branches of arbitrary length and width were drawn connecting different original branches together. One mask has a sparse arrangement of new branches, one has moderate branching, and the last one has major branching. This branching was determined randomly in an effort to mimic angiogenesis of blood vessels in vivo. In order to quantify this and compare devices, we calculated the "vascular" volume of each device and report it as a percentage of vascularity, defined as the vascular volume divided by the tissue volume. Since these fabricated devices are only branches with no physical tissue volume present, we substituted the value for the tissue volume we have designed for in future experiments, which is 1 $cm^3$, or 1 mL. FIG. 4 shows operation of vascular monitoring system manifold device. FIG. 5 shows a table that can demonstrate cylindrical cross section channels. FIG. 6 shows a table that can demonstrate Rectangular Cross Section Channels FIG. 7 shows photolithography mask designs. High resolution PDF's were sent to a printing company to print these masks on transparent mylar film.

Conclusions

The instrumented manifold device can control and monitor fluid perfusion in a vascularized microphysiological model. The device solves the current unmet need of integrated vasculature for microphysiological model systems. The mathematical theory supporting the MPM allows for the creation of many diverse kinds of vascularized systems, such as different vessel densities for distinct organ systems, and can even be used to monitor angiogenesis and anastomosis over time. This platform can be used to quickly and conveniently study different fluid dynamics scenarios, like shear stress and pressure, and how this affects cell growth and function. The platform can also support any vascularized tissue of interest. In depth study of the physiological phenomena at the tissue level, and the interactions of those tissues with the underlying endothelial cells in the blood vessels, is now possible with our device. We believe that our system is an excellent supplement to current biosynthetic vascularized organ models.

References to Example 1

[1] H. Lee, M. Chung, and N. L. Jeon, "Microvasculature: An essential component for organ-on-chip systems," MRS Bulletin, vol. 39, pp. 51-59, 2014.
[2] W. Zhang, Y. S. Zhang, S. M. Bakht, J. Aleman, S. R. Shin, K. Yue, et al., "Elastomeric free-form blood vessels for interconnecting organs on chip systems," Lab Chip, vol. 16, pp. 1579-86. Apr. 26 2016.
[3] Y. Zheng, J. Chen, M. Craven, N. W. Choi, S. Totorica, A. Diaz-Santana, et al., "In vitro microvessels for the study of angiogenesis and thrombosis," Proc Natl Acad Sci USA, vol. 109, pp. 9342-7, Jun. 12 2012.
[4] J. S. Miller, K. R. Stevens, M. T. Yang, B. M. Baker, D. H. Nguyen, D. M. Cohen, et al., "Rapid casting of patterned vascular networks for perfusable engineered three-dimensional tissues," Nat Mater, vol. 11, pp. 768-74, September 2012.
[5] S. A. Roberts, K. A. DiVito, F. S. Ligler, A. A. Adams, and M. A. Daniele, "Microvessel manifold for perfusion and media exchange in three-dimensional cell cultures," Biomicrofluidics, vol. 10, p. 054109, September 2016.

[6] Y. S. Zhang, F. Davoudi, P. Walch, A. Manbachi, X. Luo, V. Dell'Erba, et al., "Bioprinted thrombosis-on-a-chip," Lab Chip, vol. 16, pp. 4097-4105, Oct. 18 2016.

[7] X. Wang, D. T. Phan, A. Sobrino, S. C. George, C. C. Hughes, and A. P. Lee, "Engineering anastomosis between living capillary networks and endothelial cell-lined microfluidic channels," Lab Chip, vol. 16, pp. 282-90, Jan. 21 2016.

[8] J. A. VVhisler, M. B. Chen, and R. D. Kamm, "Control of perfusable microvascular network morphology using a multiculture microfluidic system," Tissue Eng Part C Methods, vol. 20, pp. 543-52, July 2014.

[9] S. Kim, H. Lee, M. Chung, and N. L. Jeon, "Engineering of functional, perfusable 3D microvascular networks on a chip," Lab Chip, vol. 13, pp. 1489-500, Apr. 21 2013.

[10] M. R. Zanotelli, H. Ardalani, J. Zhang, Z. Hou, E. H. Nguyen, S. Swanson, et al., "Stable engineered vascular networks from human induced pluripotent stem cell-derived endothelial cells cultured in synthetic hydrogels," Acta Biomater, vol. 35, pp. 32-41, Apr. 15 2016.

[11] M. L. Moya, Y. H. Hsu, A. P. Lee, C. C. Hughes, and S. C. George, "In vitro perfused human capillary networks," Tissue Eng Part C Methods, vol. 19, pp. 730-7, September 2013.

[12] M. A. Daniele, A. A. Adams, J. Naciri, S. H. North, and F. S. Ligler, "Interpenetrating networks based on gelatin methacrylamide and PEG formed using concurrent thiol click chemistries for hydrogel tissue engineering scaffolds," Biomaterials, vol. 35, pp. 1845-56, February 2014.

Example 2

The fundamental concept behind our design is that given an inlet and outlet reservoir of fluid, branching conduits in parallel to each other will all have the same pressure drop. Our system is analogous to a parallel circuit, in which all parallel resistors have the same voltage drop. Therefore, the basic equation that describes this phenomenon in fluid dynamics is, $\Delta P = Q * R_h$, where $\Delta P$ is pressure drop, Q is flow rate, and Rh is hydrodynamic resistance. In our system, assuming the hydrodynamic resistance of the inlet and outlet reservoirs are orders of magnitude smaller than that of the pressure jumper (which it is), the total hydrodynamic resistance is, $$\frac{1}{R_h} = \frac{1}{R_j} - \frac{N_v}{R_v},$$

where Rj is the hydrodynamic resistance of the pressure jumper, $N_v$ is the number of vessels in the scaffold, and $R_v$ is the hydrodynamic resistance of a vessel. This gives us a new equation for pressure drop, $$\Delta P = Q_{tot} * \left( \frac{1}{R_j} + \frac{N_v}{R_v} \right)^{-1},$$

that depends on the hydrodynamic resistances of the branches and the flow rate going into the system. As the predefined vessels proliferate and anastomose, Nv increases which means the pressure drop in the system will decrease, which will be detected via a decrease in flow rate in the jumper since the jumper resistance will not change but the pressure will. This feedback will be used to correlate the perfusion to total vascularization and maintain optimal perfusion pressures.

The FIGS. 9A-11 can detail the mathematical simulation of device, which illustrates the proof of operating principle. Included is also a photograph of the current prototype. Additional data and figures can be provided upon request.

Figure 10:
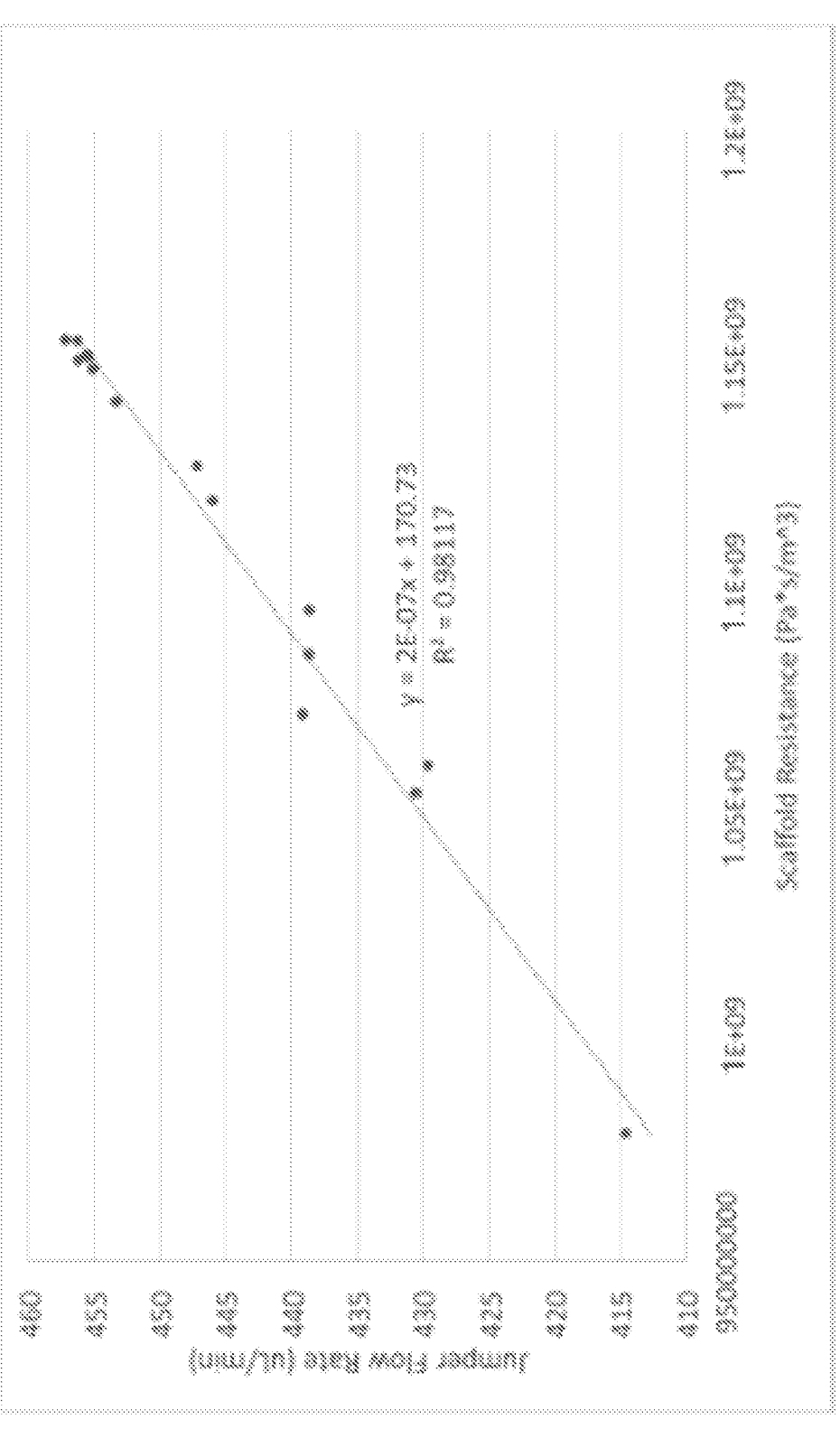
FIG. 10 shows a graph that can demonstrate the relationship between scaffold resistance and flow rate through the jumper.
Figure 12:
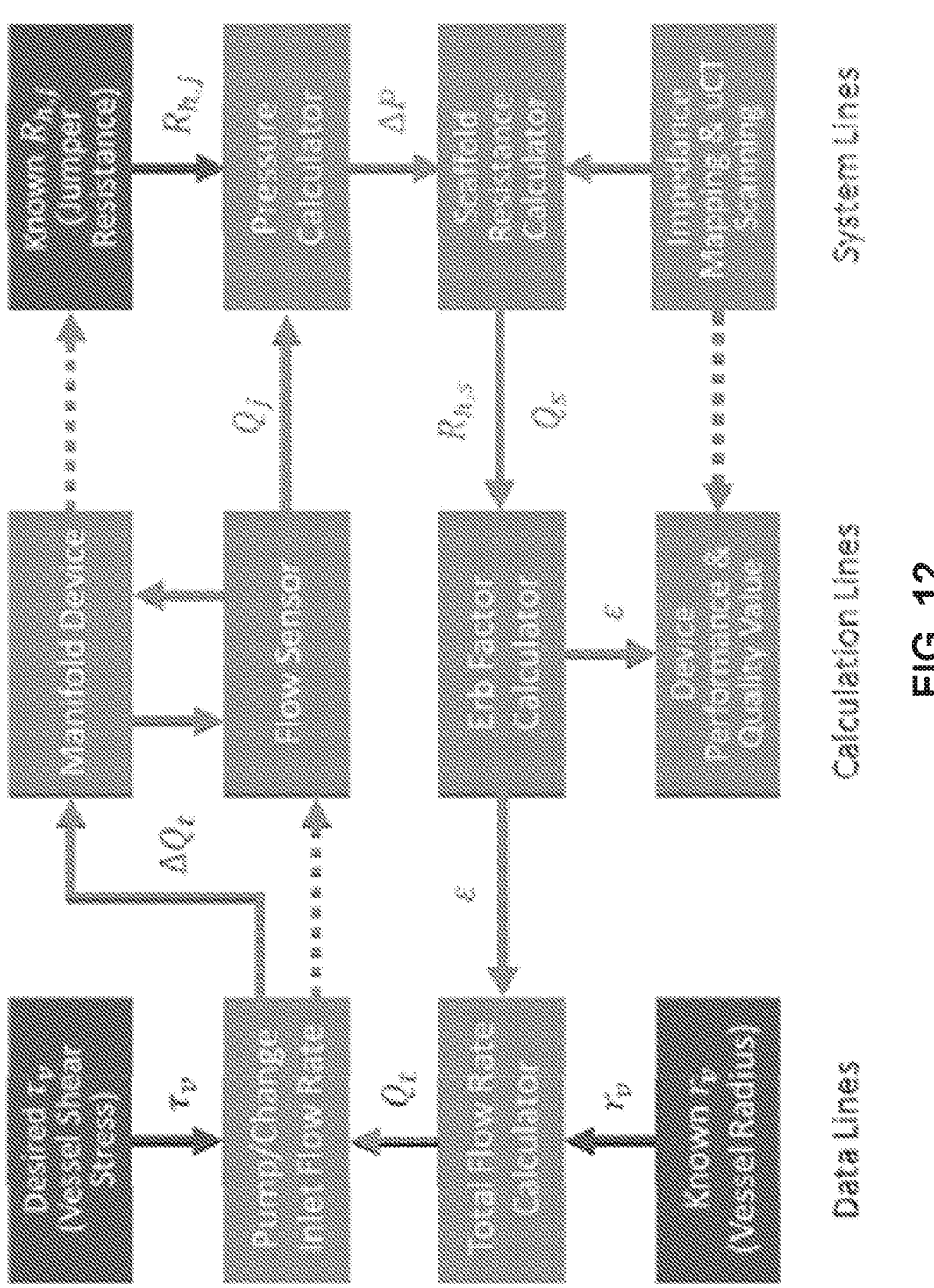
FIG. 12 shows steps for measuring, quantifying, and controlling the vascularization of an engineering tissue based on perfusion monitoring.

FIGS. 9A-9LL show heat maps from COMSOL which demonstrate the geometry that was simulated to evaluate the relationship between decreasing scaffold resistance (parallel conduits) and flow rate in the jumper (curved path). The scaffold resistance decreases as more connections are made to the original parallel conduits, which translates into a decrease in flow rate through the jumper. FIG. 10 can demonstrate this relationship. It is the flow rate within a jumper that is being measured by a sensor and a feedback loop allows for control over this system to regulate fora constant pressure, shear stress, flow rate, or other fluid parameter. FIG. 11 shows an image of a mock manifold device under operation, complete with a flow sensor on the jumper and a peristaltic pump for fluid flow from the inlet to the outlet. FIG. 12 shows steps for measuring, quantifying, and controlling the vascularization of an engineering tissue based on perfusion monitoring.

We claim:

1. A system configured to monitor, control, or monitor and control vascular development in a microfluidic device, the system consisting of:
   a manifold device comprising:
      an inlet reservoir comprising an inlet configured to receive a fluid flow with a first hydrodynamic resistance;
      an outlet reservoir comprising an outlet configured to drain the fluid flow from the manifold device with a second hydrodynamic resistance;
      a vascularized scaffold block having a plurality of parallel vessels fluidly coupled to the inlet reservoir and the outlet reservoir;
      a pressure jumper fluidly coupled to the inlet reservoir and the outlet reservoir in parallel with the plurality of parallel vessels with a third hydrodynamic resistance;
      a sensor coupled to the pressure jumper configured to measure fluid flow rate, pressure, or a combination thereof through the pressure jumper; and
      a pump fluidly coupled to the inlet and the outlet of the manifold device; and
      a computer configured to receiving and analyze data from the sensor and control the fluid flow rate and/or pressure of the pump,
      wherein the third hydrodynamic resistance in the pressure jumper is greater than the first hydrodynamic resistance in the inlet reservoir and the second hydrodynamic resistance in the outlet reservoir,
      wherein a decrease in resistance in the plurality of parallel vessels decreases the flow rate through the pressure jumper, and wherein an increase in resistance in the plurality of parallel vessels increases the flow rate through the pressure jumper;
      wherein the computer is configured to increase or decrease the amount of fluid in the fluid flow of the system in response to changes in fluid flow rate and/or pressure through the pressure jumper.

2. The system of claim 1, wherein the pressure jumper is semi-toroid in shape.

3. The system of claim 1, wherein the first and second hydrodynamic resistances are each orders of magnitude smaller than the third hydrodynamic resistance.

4. A system configured to monitor, control, or monitor and control vascular development in a microfluidic device, the system consisting of:

a manifold device comprising:

an inlet reservoir comprising an inlet configured to receive a fluid flow with a first hydrodynamic resistance;

an outlet reservoir comprising an outlet configured to drain the fluid flow from the manifold device with a second hydrodynamic resistance;

a vascularized scaffold block having a plurality of parallel vessels fluidly coupled to the inlet reservoir and the outlet reservoir;

a pressure jumper fluidly coupled to the inlet reservoir and the outlet reservoir in parallel with the plurality of parallel vessels with a third hydrodynamic resistance;

a fluid that flows through the inlet reservoir, pressure jumper, and outlet reservoir;

a sensor coupled to the pressure jumper configured to measure fluid flow rate, pressure, or a combination thereof through the pressure jumper; and a pump fluidly coupled to the inlet and the outlet of the manifold device; and a computer configured to receiving and analyze data from the sensor and control the fluid flow rate and/or pressure of the pump, wherein the third hydrodynamic resistance in the pressure jumper is greater than the first hydrodynamic resistance in the inlet reservoir and the second hydrodynamic resistance in the outlet reservoir, wherein a decrease in resistance in the plurality of parallel vessels decreases the flow rate through the pressure jumper, and wherein an increase in resistance in the plurality of parallel vessels increases the flow rate through the pressure jumper;

wherein the computer is configured to increase or decrease the amount of the fluid in the fluid flow of the system in response to changes in fluid flow rate and/or pressure through the pressure jumper.

5. The system of claim 4, wherein the first and second hydrodynamic resistances are each orders of magnitude smaller than the third hydrodynamic resistance.

* * * * *